United States Patent [19]

Fahrenholtz et al.

[11] 4,336,382
[45] Jun. 22, 1982

[54] 1,4-DISUBSTITUTED PIPERAZINE COMPOUNDS

[75] Inventors: Kenneth E. Fahrenholtz, Bloomfield; Robert W. Guthrie, Saddle Brook; Richard W. Kierstead; Jefferson W. Tilley, both of North Caldwell, all of N.J.

[73] Assignee: Hoffmann-La Roche Inc., Nutley, N.J.

[21] Appl. No.: 181,256

[22] Filed: Aug. 25, 1980

Related U.S. Application Data

[62] Division of Ser. No. 73,051, Jun. 6, 1979, Pat. No. 4,247,710, which is a division of Ser. No. 875,966, Feb. 8, 1978, Pat. No. 4,206,129.

[51] Int. Cl.³ .......................................... C07D 405/10
[52] U.S. Cl. .................................... 544/374; 424/250; 544/393; 544/394; 260/456 R; 560/264; 560/266; 562/430; 562/452; 562/472; 562/607; 564/93; 568/644; 568/649; 568/651
[58] Field of Search ........................ 544/374, 393, 394

[56] References Cited

U.S. PATENT DOCUMENTS

| | | | |
|---|---|---|---|
| 3,029,241 | 4/1962 | Fancher et al. | 544/393 |
| 3,211,735 | 10/1965 | de Stevens et al. | 544/394 |
| 3,270,004 | 8/1966 | Alter | 544/394 |
| 3,701,777 | 10/1972 | Edenhofer et al. | 544/394 |
| 3,965,106 | 6/1976 | Maruyama et al. | 544/394 |

FOREIGN PATENT DOCUMENTS

| | | | |
|---|---|---|---|
| 3864M | 4/1964 | France | 544/394 |
| 984017 | 2/1965 | United Kingdom | 544/394 |
| 1166595 | 10/1969 | United Kingdom | 544/393 |

*Primary Examiner*—Donald G. Daus
*Assistant Examiner*—James H. Turnipseed
*Attorney, Agent, or Firm*—Jon S. Saxe; Bernard S. Leon; Frank P. Hoffman

[57] ABSTRACT

There are disclosed compounds of the formula

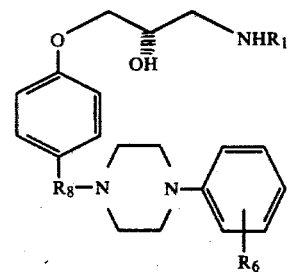

wherein $R_1$ is selected from the group consisting of lower alkyl; $R_8$ is selected from the group consisting of —O—$(CH_2)_n$—wherein n is 2 to 20, and $R_6$ is selected from the group consisting of hydrogen or lower alkoxy, and

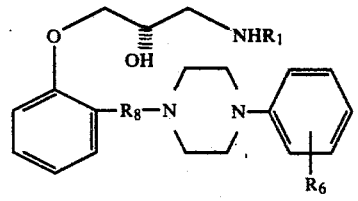

wherein $R_1$ is selected from the group consisting of lower alkyl; $R_8$ is selected from the group consisting of —O—$(CH_2)_n$—wherein n is 2 to 20, and $R_6$ is selected from the group consisting of hydrogen or lower alkoxy and racemates thereof.

There are also disclosed processes and intermediates utilized to produce the end products.

The end products have utility as agents exhibiting both α and selective β adrenergic blocking action.

11 Claims, No Drawings

1,4-DISUBSTITUTED PIPERAZINE COMPOUNDS

This is a division of application Ser. No. 73,051 filed Sept. 6, 1979, now U.S. Pat. No. 4,247,710 which in turn is a divisional of U.S. patent application Ser. No. 875,966, filed Feb. 8, 1978, now U.S. Pat. No. 4,206,129, issued June 3, 1980.

DESCRIPTION OF THE INVENTION

The present invention relates to binary $\alpha\beta$-Adrenergic Blocking Agents of the formula

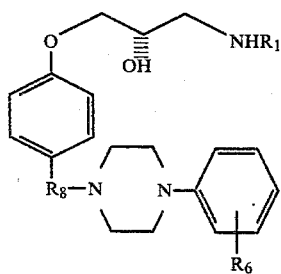

wherein $R_1$ is selected from the group consisting of lower alkyl; $R_8$ is selected from the group consisting of $-O-(CH_2)_n-$ wherein n is 2 to 20,

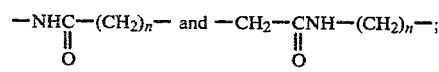

and $R_6$ is selected from the group consisting of hydrogen or lower alkoxy, and

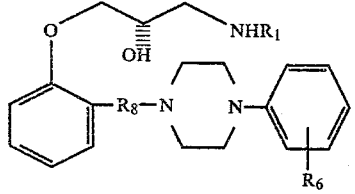

wherein $R_1$ is selected from the group consisting of lower alkyl; $R_8$ is selected from the group consisting of $-O-(CH_2)_n-$ wherein n is 2 to 20,

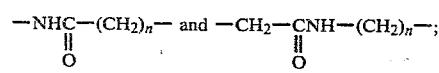

and $R_6$ is selected from the group consisting of hydrogen or lower alkoxy and the racemates thereof The presently disclosed and claimed compounds exhibit both $\alpha$ and $\beta$-adrenergic blocking activities which are essential to their use as antihypertensive agents. They provide competitive and reversible blockade of both $\alpha$ and $\beta$ adrenoreceptors and have the unexpected property of being cardioselective, having low activity at one site ($\beta_2$) and good activity at the $\beta_1$ site. This selectivity has important consequences when selecting an antihypertensive agent. Further the compounds have exhibited anti-secretory, i.e. spasmolytic activity.

By the term "lower alkyl" is meant straight or branched chains of $C_1$ to $C_{10}$ length with branched chains of $C_3$ to $C_4$ as preferred, e.g., isopropyl or tertiary butyl.

By the term "lower alkoxy" is meant straight or branched chain saturated hydrocarbonoxy groups containing from 1 to 7 carbon atoms, preferably 1 to 4 carbon atoms such as methoxy, ethoxy, propoxy and the like.

The term "halo" or "halogen" refers to all four forms thereof, i.e., bromine, chlorine, fluorine or iodine with bromine and chlorine as preferred.

It should be noted that the racemates of the above compounds are also novel and exhibit activities similar to the preferred (S) isomers although not as quantitatively active. The racemates may also be resolved into the desired isomers when desired.

The following reaction schemes represent the methods of synthesis available to produce the novel end compounds of the present invention:

SCHEME I

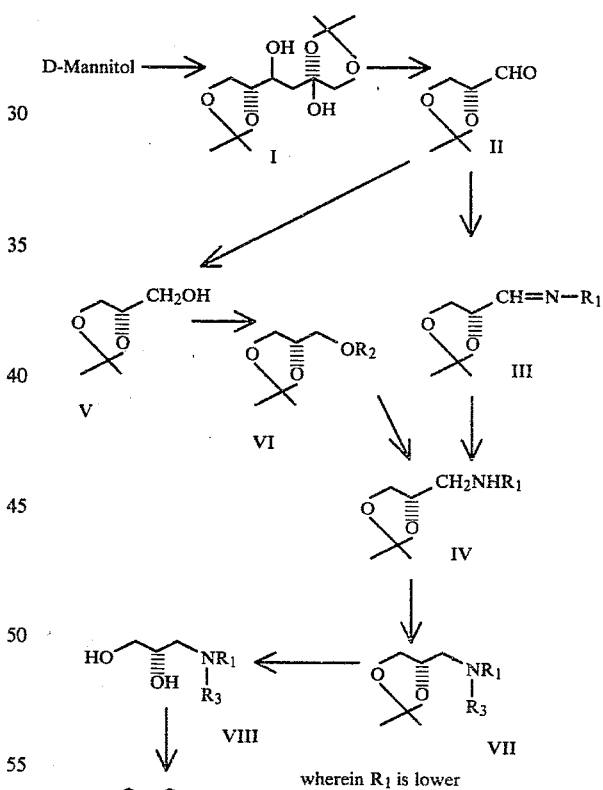

wherein $R_1$ is lower alkyl, $R_2$ and $R_3$ are selected from the group consisting of hydrogen, mesyl, tosyl, brosyl or benzenesulfonyl and $R_4$ is selected from the group consisting of halo, mesyloxy or tosyloxy

SCHEME 2

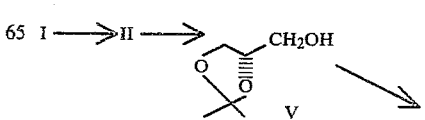

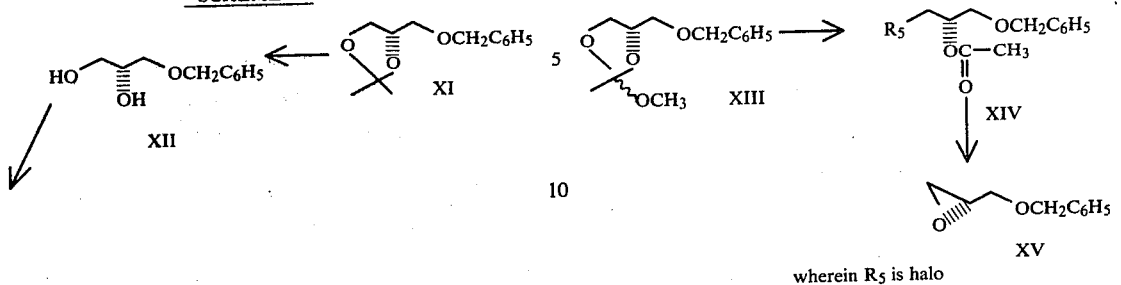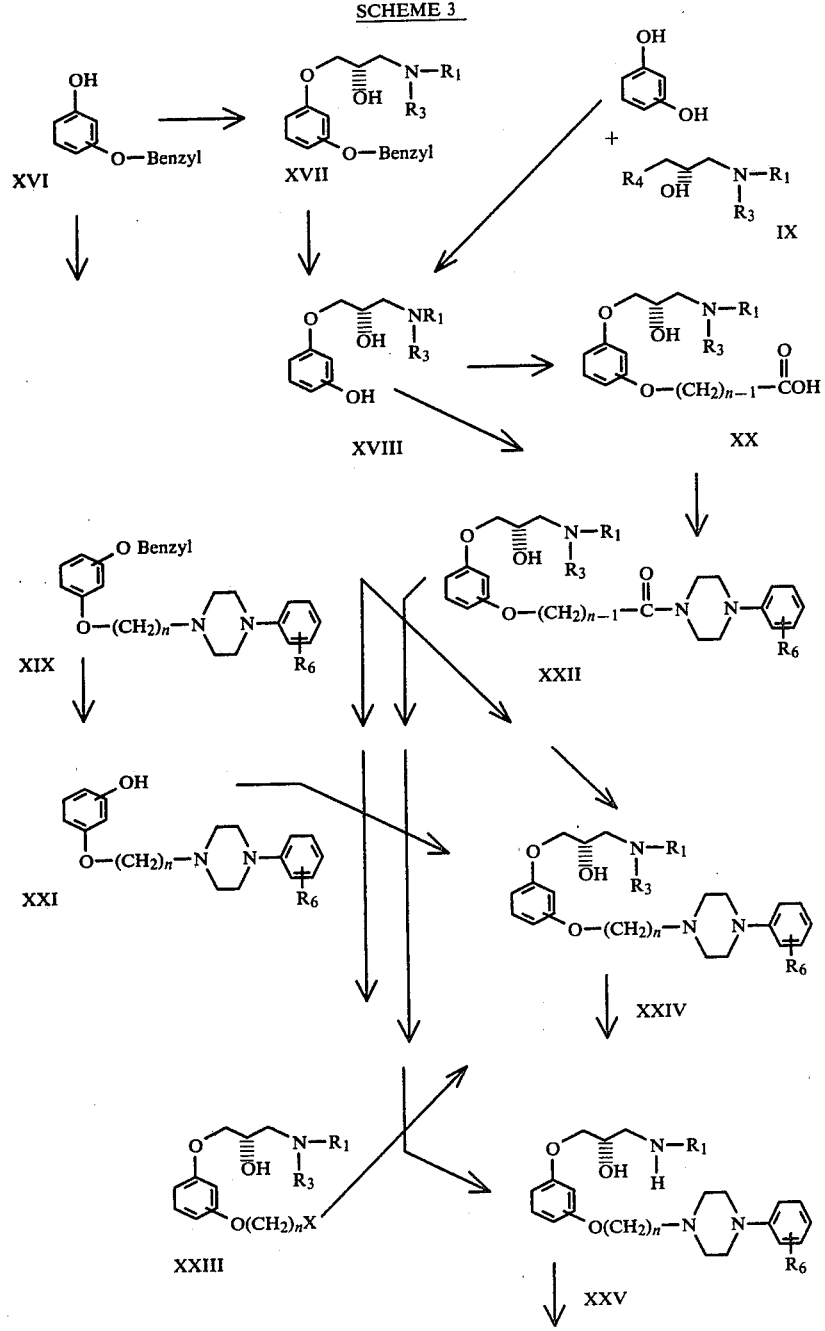

SCHEME 3
wherein $R_1$ and $R_2$ are as above, $R_6$ is hydrogen or lower alkoxy, n is 2 to 20 and X is also halo
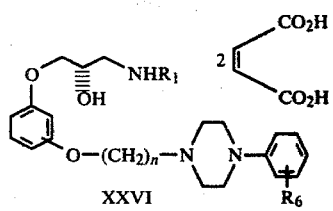
SCHEME 4
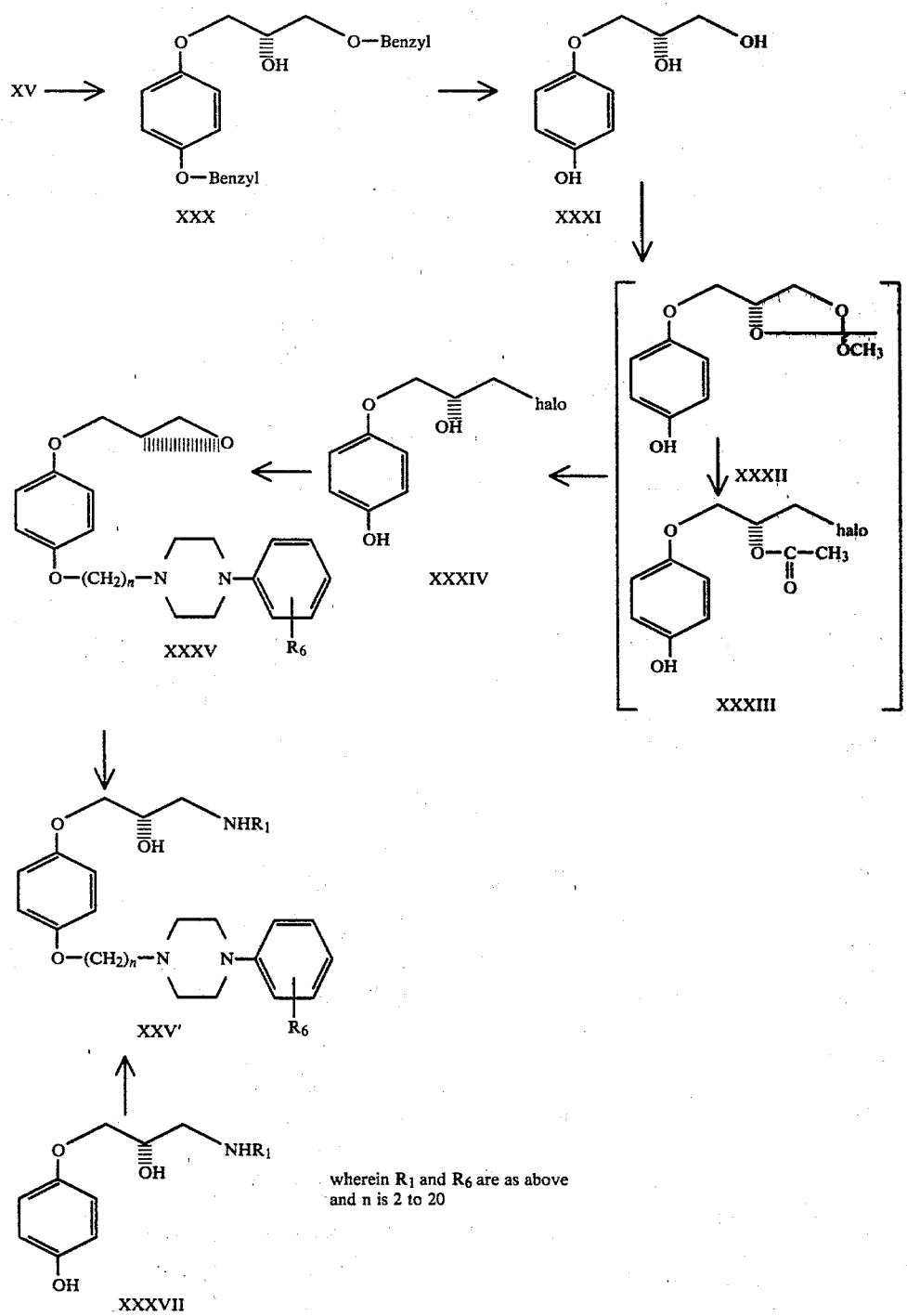
wherein $R_1$ and $R_6$ are as above and n is 2 to 20

4,336,382
-continued
SCHEME 4
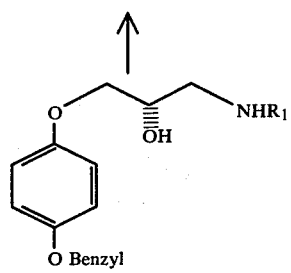
XXXVI
XVII
SCHEME 5
SCHEME 6
(Racemic Series)
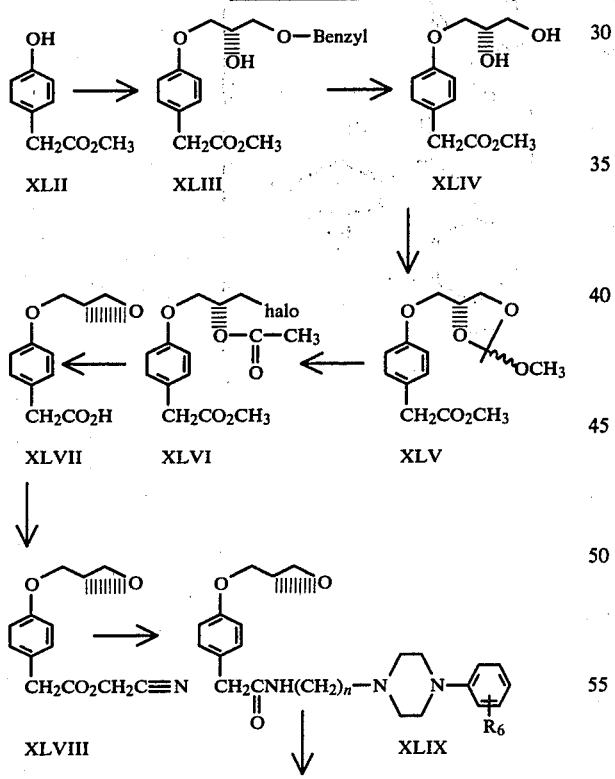
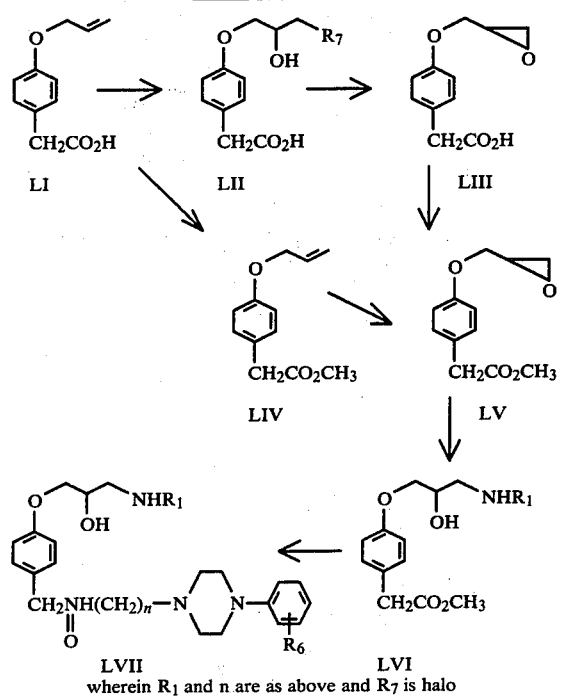
LVII
wherein $R_1$ and n are as above and $R_7$ is halo
L
wherein $R_1$ and $R_6$ are as above and n is 2 to 20
SCHEME 7
(Racemic Series)
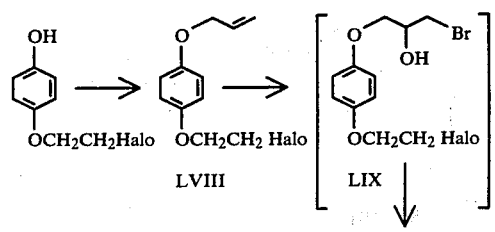

-continued
SCHEME 7
(Racemic Series)
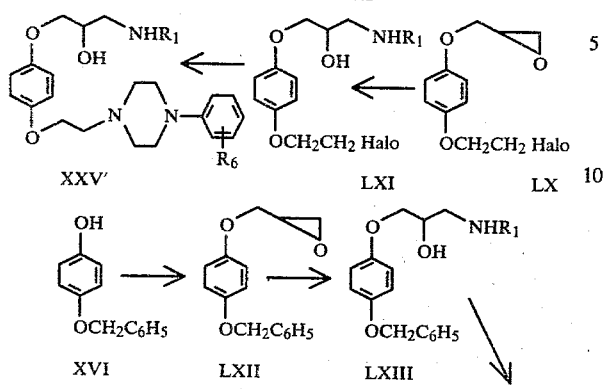
-continued
SCHEME 7
(Racemic Series)
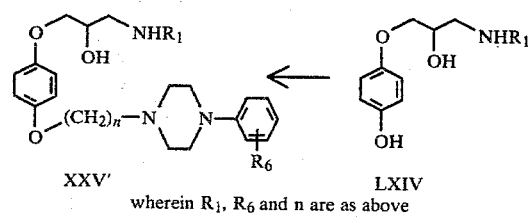
wherein $R_1$, $R_6$ and n are as above
SCHEME 8
(Racemic Series)
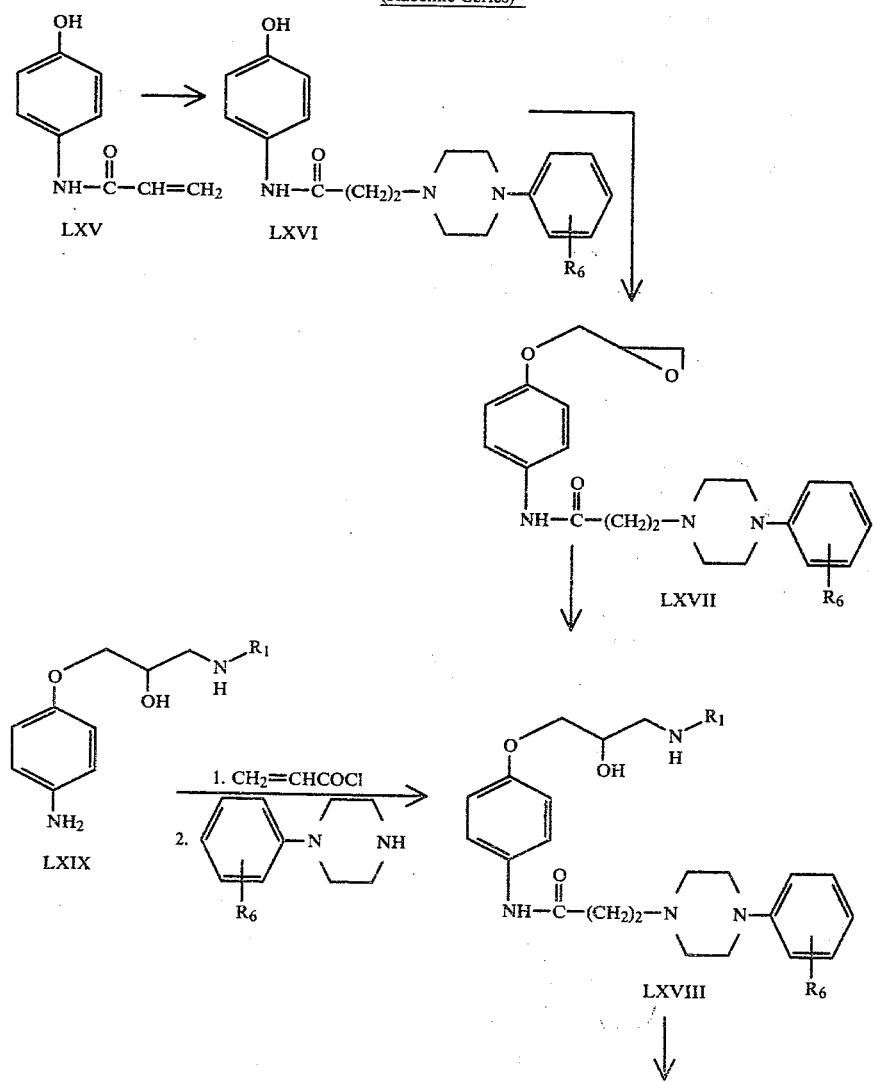

SCHEME 8
(Racemic Series)

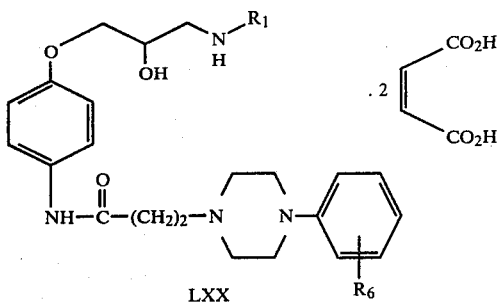

wherein $R_1$ and $R_6$ are as above

SCHEME 9
(Racemic Series)

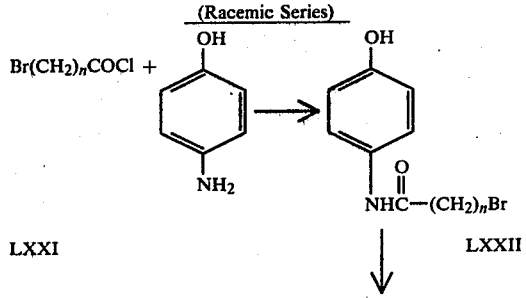

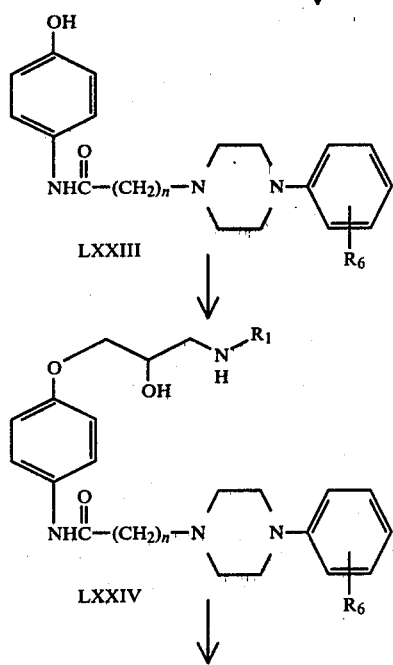

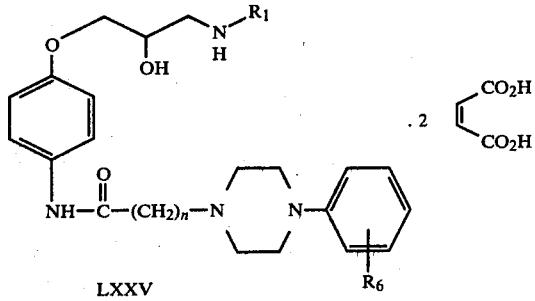

-continued
SCHEME 9
(Racemic Series)

wherein $R_1$, $R_6$ and n are as above

D-Mannitol→I

The compound of formula I which is a known compound is produced by utilizing an acid catalyzed ketal exchange reaction. The reaction is carried out utilizing a strong mineral acid, such as, sulfuric acid or p-toluenesulfonic acid or a cation exchange resin. The reaction is carried out at a temperature range of about 0° C. to 100° C. with room temperature as preferred. The time of the reaction to completion will vary from 1 to 16 hours depending on the reaction temperature selected.

I→II→V

The two step reaction to produce the compound of formula V is a known reaction, see, for example, J. Lecocq and C. E. Ballou, Biochemistry, 3, 976, (1964).

V→VI

The compound of formula VI is produced by reaction of the primary alcohol (V) with a lower alkyl or aryl sulfonyl halide in the presence of a tertiary amine base. Examples of lower alkyl or aryl sulfonyl halides which may be used are mesyl, tosyl, brosyl or benzylsulfonyl chlorides or bromides. Examples of tertiary amine bases include pyridine or trialkylamines, e.g. tri-n-butyl or triethylamines. An inert solvent may be utilized to facilitate the reaction such as methylene chloride or tetrahydrofuran or pyridine. The latter functions as both reactant and solvent. The reaction temperature may vary from about −25° C. to 15° C. with −10° C. to 15° C. as preferable and 0° C. to 15° C. as optimum. The reaction time may range from 30 minutes to 1 hour depending on the reaction temperature chosen.

VI→IV

The compound of formula IV is thereafter produced by displacement of the leaving group (the alkyl or arylsulfonyloxy group) using a primary amine such as a methyl, ethyl, isopropyl or tertiary butyl amine. The reaction can be performed with or without an inert solvent (benzene, lower alcohols or ethers may be employed). In the case of lower boiling amines, e.g. isopropylamine, the reaction should be run in a pressurized vessel. The reaction temperature may vary from room temperature to about 150° C. with approximately 100° C. as the preferred temperature.

I→II→III→IV

A multistep sequence may also be utilized to produce a compound of formula IV in which the intermediates II and III are not isolated. The compound of formula I is oxidized to II utilizing lead tetraacetate in an inert aromatic hydrocarbon solvent, such as, benzene, toluene or xylene. The reaction temperature should be kept at room temperature or below, e.g., 0° C. After one side product, Pb(OAc)$_2$, has been removed by filtration, the acetic acid which has been generated in the reaction is neutralized by the addition of an alkali metal (Na, K, etc.) carbonate or oxide, e.g., BaO.

The aldehyde (II) is thereafter reacted with a large excess of a primary amine, e.g. methyl, ethyl, isopropyl, etc. amine to form the imine (III). The reaction temperature should be at about 25° C. or less and a desiccant, e.g. K$_2$CO$_3$, should be used to remove any water formed and drive the reaction to completion.

Thereafter the imine (III) is hydrogenated to the secondary amine (IV) by the use of a catalyst such as noble metals (Platinum, Palladium, Ruthenium, etc.) on carbon or Raney Nickel/H$_2$ under pressure. This reaction may be carried out at 20° C.-50° C. with room temperature as preferred. The reaction may be run at 1 to 10 atmospheres depending on the catalyst chosen.

IV→VII

The amine (IV) is thereafter reacted with an alkyl or aryl sulfonyl halide such as a mesyl, tosyl, brosyl or benzylsulfonyl chloride or bromide in an inert aprotic solvent such as high boiling ethers, e.g., dioxane, tetrahydrofuran or methylene chloride in the presence of a tertiary amine base, e.g., triethyl or trimethylamine. The reaction is carried out at a temperature range of about −50° C. to 25° C. with about −10° C. to 5° C. as preferred.

VII→VIII

The compound of formula VII thereafter undergoes an acid catalyzed hydrolysis of the ketal protecting group. To effect this catalysis, strong mineral acids are utilized, e.g., HCl, H$_2$SO$_4$ or p-toluenesulfonic acid or a strongly acidic ion exchange resin (H+form). The reaction solvent may be water and a miscible co-solvent, such as, a lower alcohol (methanol, ethanol, propanol, etc.) and ethers such as tetrahydrofuran or dioxane. The reaction temperature range is from about room temperature to 80° C. with about 60° C. to 80° C. as preferred. The reaction time may range from 1 hour to 2 days depending on the temperature selected.

VIII→IX

The diol of formula VIII is thereafter reacted with an alkyl or aryl sulfonyl halide (as previously disclosed in step V→VI) in the presence of a tertiary amine base (also disclosed in V→VI) wherein the primary hydroxyl group is selectively converted into an alkyl or aryl sulfoxy group. As disclosed previously in step V→VI pyridine may serve as the base and solvent or other previously disclosed solvents may be utilized (V→VI). The reaction temperature ranges (depending on what sulfonyloxy group) is desired may vary from about −45° C. to −50° C. (mesyl) to −5° C. to 5° C. (tosyl). When R$_4$ of formula IX is to be halo the reaction will differ from above. The compound of formula VIII undergoes an acid catalyzed exchange reaction with a trialkylorthoacetate, e.g., trimethyl, triethyl, etc. to give the cyclic orthoacetate of the formula

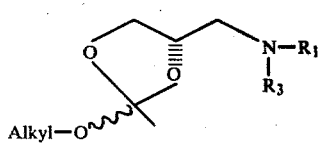

and alkanol. The alkanol is distilled from the reaction mixture as formed to facilitate reaction completion. No solvents are necessary for the reaction. The reaction temperature ranges from about 60° C. to 100° C. with 80° C. as preferred. The time of the reaction varies from 30 minutes to 1 hour depending on the reaction temperature. The cyclic orthoacetate is thereafter reacted with trimethylhalosilane in an inert, aprotic solvent, such as, methylene chloride, giving rise to the intermediate of the formula

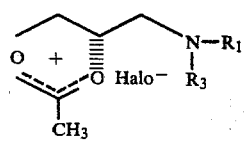

which on attack by the halide ion gives the haloacetate. As solvents for this step, inert aprotic solvents such as high boiling ethers and halogenated hydrocarbons, e.g., methylene chloride, are best. The reaction may be run from about room temperature to reflux temperature for about 30 minutes. A reaction temperature of 40° is preferred. Thereafter the haloacetate is reacted in an acid catalyzed hydrolysis. To carry out the reaction a solution of the substrate in a hydrolytic solvent such as alcohols, e.g., methanol, ethanol, propanol etc. or aqueous alcohol mixtures containing a catalytic amount of a mineral acid such as HCl, H$_2$SO$_4$ or an acidic ion exchange resin are utilized. The reaction temperature may be varied from 0° C. to reflux temperature (solvent dependent) for 30 minutes to 16 hours. Room temperature is preferred.

I→II→V

This procedure is carried out as disclosed previously by a prior art method.

V→XI

The hydroxyl group of the compound of formula V is protected as its benzyl ether by producing the compound of the formula XI. The reaction is one of the alcohol (V) with an alkali metal hydride, e.g., Na, Li, K, etc., to form the alkoxide which then is reacted with an alkylating agent, i.e. a benzyl halide (Cl or Br) to give the benzyl ether (XI). Solvents suitable for such a reaction include anhydrous dimethylformamide, dimethylsulfoxide and high boiling ethers such as tetrahydrofuran or dioxane. The reaction temperature may range from about room temperature to 100° C. with about room temperature as preferred.

XI→XII

The compound of formula XII is thereafter produced by an acid catalyzed hydrolysis of the ketal protecting group. Reagents and reaction parameters are the same as in previously disclosed step VII→VIII.

XII→XIII→XIV

The diol of formula XII is converted into the haloacetate of formula XIV via the compound of formula XIII and the intermediate of the formula

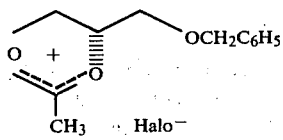

by following the steps and utilizing the reactants and reaction parameters disclosed previously in step VIII→IX. This series of reactions are performed because selective alkyl or aryl sulfonyloxy of the primary hydroxyl group in XII is difficult due to the similar reactivity of both of the hydroxyl groups in XII.

XIV→XV

The compound of formula XIV thereafter undergoes a two step reaction wherein the acetate (XIV) is saponified to give the intermediate halohydrin of the formula

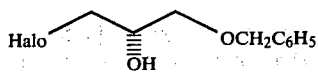

which is then converted under basic conditions into the epoxide of formula XV. The reaction is carried out utilizing an alkali metal, e.g., Na or K, hydroxide in a solvent of $H_2O$ plus an inert water miscible co-solvent such as a lower alcohol, e.g., methanol, ethanol, propanol, etc. The reaction temperature may vary from about $-10°$ C. to $25°$ C. with a range of about $0°$ C. to $10°$ C. as preferred. It should be noted that the above reactions preserve the stereochemistry of the asymmetric carbon atom throughout.

XVI→XVII

This reaction is a two step sequence wherein a compound of the formula IX under basic reaction conditions is converted into the epoxide of the formula

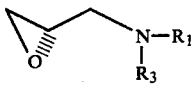

wherein $R_1$ and $R_3$ are as above. This compound acts as the alkylating agent in the ensuing reaction with the phenol (XVI) under basic catalysis conditions to form the ether (XVI). The base utilized in the reaction is an alkali metal hydroxide, e.g., NaOH or KOH and the reaction temperature ranges from about room temperature to $100°$ C. The reaction time may vary from about 2 hours to several days depending on the reaction temperature chosen. The solvents utilized may be dimethylsulfoxide, tetrahydrofuran and lower alcohol/water mixtures.

HYDROXYPHENOL→XVII

This reaction is similar to XVI→XVII except a large excess of hydroxyphenol is utilized to minimize any dialkylation which might occur. As in XVI→XVII the effective alkylating agent is the epoxide (see above). The reagents and reaction parameters are as above (XVI→XVII).

XVII→XVIII

The compound of formula XVII thereafter undergoes hydrogenolysis to a compound of formula XVIII. Catalysts for the reaction may be noble metals such as Platinum, Palladium, Rhodium or Ruthenium on carbon. Suitable solvents include lower alcohols (methanol, ethanol, etc.), esters (ethyl or butyl acetate) and ethers (dioxane or tetrahydrofuran). The reaction temperature may be varied from about $0°$ C. to $100°$ C. with room temperature preferred.

XVI→XIX

This reaction consists of the O-alkylation of the phenol of formula XVI with a compound of the formula

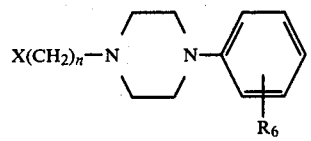

wherein X is a leaving group selected from the group consisting of halogen, tosyloxy and mesyloxy, $R_6$ is hydrogen or alkoxy and n is 2 to 20, utilizing an alkali metal hydroxide (NaOH, KOH, etc.) in an inert water miscible solvent, e.g., a dimethylsulfoxide/$H_2O$ mixture. The reaction temperature may vary from about room temperature to $60°$ C. with $60°$ C. as preferred with a reaction time from 1-2 hours to several days depending on the reaction temperature. Alternate O-alkylation systems which may be utilized in conjunction with the phenylpiperazine include alkali metal alkoxides in lower alcohols e.g., sodium methoxide in methanol or potassium carbonate in acetone.

XVIII→XXIII

The compound of formula XVIII is reacted with a compound of the formula

wherein X and Y are the same or different leaving groups with X as above and Y selected from the same leaving groups as X.

The reaction which is an O-alkylation of a phenol (XVIII) with an $\alpha,\omega$-dihaloalkane (for example) is carried out utilizing an alkali metal carbonate, such as, potassium or sodium carbonate in, as preferred, refluxing acetone. The reaction temperature may vary from room temperature to reflux with reflux as preferred.

XVIII→XXIV

This reaction follows the same reaction parameters and utilizes the same reagents as previously disclosed in step XVI→XIX.

XVIII→XX

The compound of formula XVIII is thereafter reacted with a compound of the formula

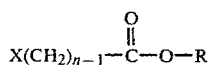

wherein X is as above and R is lower alkyl.

This O-alkylation of the phenol (XVIII) with the alkyl ω-haloalkanoate, for example, ethyl-6-bromohexanoate or ethyl bromoacetate, using as a base an alkali metal alkoxide, such as, potassium tert-butoxide, methoxide or ethoxide in a lower alcohol, e.g., methanol, ethanol, etc., at a temperature range of about 0° C. to 100° C. with 60° C. to 80° C. as preferred. The product is subsequently saponified to give the acid (XX). The saponification is usually carried out at between room temperature to 65° C. for a period of 3 to 40 hours.

XVIII→XXII

The compound of the formula XVIII is reacted with an alkylating agent of the formula

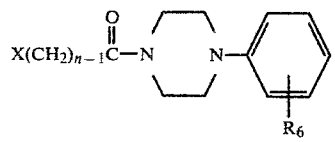

wherein X, n and $R_6$ are as before, such as, 1-(ω-haloalkanoyl)-4-phenylpiperazine, in an alcohol/water mixture or tetrahydrofuran or dimethylsulfoxide/water mixture containing an alkali metal hydroxide, e.g., NaOH or KOH. The reaction is carried out at from about room temperature to 100° C. with 75° C.-80° C. as preferred.

XIX→XXI→XXIV

The compound of formula XIX undergoes hydrogenolysis of the benzyl ether portion by utilizing a noble metal catalyst, e.g., Palladium, Platinum, Rhodium, etc. on carbon. The solvent for such a reaction may be an alcohol (methanol, ethanol, etc.) or acetic acid containing a small amount of mineral acid such as HCl or $H_2SO_4$. The reaction temperature may vary from about 0° C.-100° C. with room temperature as preferred. The compound of formula XXI thereafter undergoes an O-alkylation using an alkylating agent (IX) in the presence of an alkali metal hydroxide as a base. The reagents and reaction parameters for this reaction are as previously disclosed for step XVI→XVII.

XX→XXII

The acid of the formula XX is converted to the activated intermediate

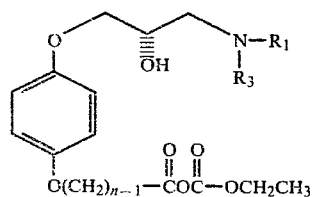

wherein $R_1$, $R_3$ and n are as above on treatment with ethyl chloroformate under anhydrous conditions in an aprotic solvent, e.g. tetrahydrofuran or dioxane, at a low temperature e.g., about 0° C. to 5° C. in the presence of a tertiary amine base, e.g. trialkylamine. This mixed anhydride is treated in situ with a phenylpiperazine of the general formula

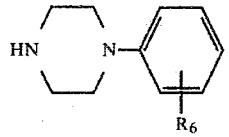

wherein $R_6$ is as above to give the tertiary amide. This reaction is carried out at between about 10° C. to 25° C.

XXIV→XXV

The compound of formula XXIV undergoes a reductive cleavage of the -$R_3$ protecting group utilizing as the reducing agent a 60–70% solution of sodium bismethoxyethoxy aluminum hydride in an inert aromatic hydrocarbon solvent such as benzene or toluene. Inert aprotic solvents such as tetrahydrofuran or dioxane may also be utilized. The reaction may be carried out at from about room temperature to 100° C. with a range of about 80° C. to 100° C. as preferred.

XXII→XXV

The compound of formula XXII undergoes a reductive cleavage of the -$R_3$ protecting group with a concommitant reduction of the amide function to an amino group. The reagents and reaction parameters for this reaction are as previously disclosed in step XXIV→XXV with the exception that a proportionately greater amount of the hydride reducing agent is employed.

XV→XXX

Suitably protected the optically active 2,3-epoxypropanol (XV) is thereafter reacted with a substituted phenol of the formula XVI in an O-alkylation using an alkali metal alkoxide, e.g., sodium or potassium methoxide or ethoxide, as the base in a lower alcohol solvent (methanol, ethanol, etc.). Also useful as a base in the above reaction would be an alkali metal hydroxide, e.g., NaOH or KOH in an aqueous alcohol, tetrahydrofuran, dioxane or dimethylsulfoxide solvent. The reaction temperature may range from room temperature to reflux for the chosen solvent with 60° C.-80° C. as preferred.

XXX→XXXI

The benzyl ethers of the formula XXX thereafter undergo a hydrogenolysis utilizing a catalyst of a noble metal such as Palladium, Platinum, Ruthenium etc. on carbon. Suitable solvents include alcohols (methanol, ethanol, propanol, etc.) or acetic acid containing a small amount of a mineral acid such as $H_2SO_4$ or HCl. The reaction temperature may range from about 0° C. to 100° C. with room temperature as preferred. The hydrogenolysis may also be run under pressure up to 10 atmospheres if a catalyst such as $H_2$/Raney Nickel is chosen.

XXXI→XXXII→XXXIII

The reagents and reaction parameters for this step have been previously disclosed in step XII→XIII→XIV.

XXXIII→XXXIV

The acetate (XXXIII) thereafter undergoes an acid catalysed hydrolysis wherein the acetate reacts in a hydrolytic solvent, such as, alcohols, e.g., methanol, ethanol, etc. or alcohol/water mixtures which contain a catalytic amount of a mineral acid such as $H_2SO_4$ or HCl or an acidic ion exchange resin. The reaction may be carried out at from about 0° C. to reflux of the chosen solvent with a range of about room temperature to 60° C. as preferred.

XXXIV→XXXV

The halohydrin (XXXIV) is therefore reacted with a phenylpiperazine of the formula

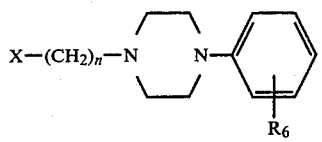

wherein X is halo.

This reaction involves two separate and unrelated base-induced transformations, i.e., (1) conversion of the halohydrin into an epoxide and (2) the O-alkylation of the phenol with the selected phenylpiperazine. The reaction is carried out under basic conditions utilizing an alkali metal hydroxide, e.g., NaOH or KOH in an aqueous dimethylsulfoxide, tetrahydrofuran or alcohol (methanol, ethanol, etc.) solvent. The reaction is carried out from about 0° C. to 40° C. with higher temperatures, e.g., 40° C. as preferred.

XXXV→XXV

The epoxide of formula XXXV is reacted with a monoalkylamine such as isopropyl, t-butyl, etc. amine to produce the amino alcohol. Solvents for such a reaction are alcohols ($C_1$–$C_4$) with methanol preferred or ethers, such as, tetrahydrofuran or dioxane. The reaction may be run from about 0° C. to 100° C. with about 65° C. as preferred.

XVII→XXXVI

The compound of formula XVII undergoes a reductive cleavage of the N-protected amine to give the secondary amine. Reagents and reaction parameters for this reaction have been previously disclosed for step XXIV→XXV.

XXXVI→XXXVII

The benzyl ether of formula XXXVI thereafter undergoes hydrogenolysis in a catalyzed reaction. Suitable catalysts include noble metals (as previously disclosed) on carbon in a solvent such as lower alcohols ($C_1$ to $C_4$) e.g., methanol or ethanol at a temperature range of from about 0° C. to 100° C. If $H_2$/Raney Nickel is chosen as the catalyst, the reaction should be run under pressure, e.g., up to 10 atmospheres.

XXXVII→XXV

The phenol (XXXVII) undergoes a base induced O-alkylation with a phenylpiperazine of the formula

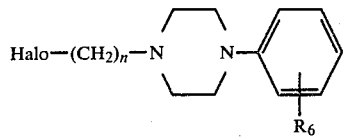

wherein n and $R_6$ are as above. in an aqueous dimethylsulfoxide, tetrahydrofuran or dioxane solvent. Suitable bases include alkali metal hydroxides, such as, NaOH or KOH. The reaction temperatures ranges from about 0° C. to 100° C. with about 60° C. as preferred.

XLII→XLIII

The compound of the formula XLII is reacted with a compound of the formula

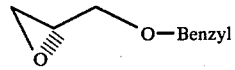

to produce the compound of the formula XLIII. The reactants and reaction parameters have been previously disclosed in step XV→XXX.

XLIII→XLIV

The compound of formula XLIII thereafter undergoes a hydrogenolysis as previously disclosed and with the same reagents and reaction parameters as step XXX→XXXI.

XLIV→XLV→XLVI

The compound of formula XLIV is converted to a compound of formula XLVI utilizing the same reagents and reaction parameters as previously disclosed in step XII→XIII→XIV.

XLVI→XLVII

The compound of formula XLVI undergoes a three step reaction under basic conditions as follows:

(A) saponification of the methyl ester (B) saponification of the acetate to give the halohydrin and (C) conversion of the intermediate halohydrin into the epoxide (XLVII). As the base, an alkali metal hydroxide, e.g., NaOH or KOH, in a solvent of water plus as inert water miscible co-solvent such a lower alcohol ($C_1$ to $C_4$) e.g., methanol or tetrahydrofuran or dioxane. The reaction is carried out from about 0° C. to 30° C. with a preferred temperature range of about 10° C. to 25° C.

XLVII→XLVIII

The activated ester of formula XLVIII is produced by treatment of the acid (XLVII) with an excess of a haloacetonitrile (Halo-$CH_2C\equiv N$) in the presence of a tertiary amine base, such as, trialkylamine, e.g., triethyl- or trimethylamine. The reaction temperature may range from about 0° C. to 70° C. with a range of about 25° C.–70° C. as preferred. The activated ester may be utilized to undergo condensation reactions, such as reactions with amines to form amides at a much faster rate than the ordinary methyl or ethyl esters.

XLVIII→XLIX

The ester of formula XLVIII is thereafter condensed with a primary amine of the formula

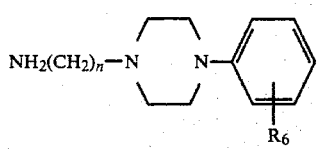

to form the amide (XLIX). An inert solvent, such as, tetrahydrofuran or dioxane, may be utilized at a temperature range of about 0° C. to 100° C. with room temperature as preferred.

XLIX→L

The epoxide of formula XLIX is thereafter reacted with a primary amine e.g., an amine of the formula $NH_2-R_1$ wherein $R_1$ is as above in a solvent, such as, $C_1$ to $C_4$ alcohols or ethers, e.g., tetrahydrofuran or dioxane, to form the amino alcohol (L). The reaction may be run at from about 0° C. to reflux temperature with room temperature to 65° C. as preferred.

LI→LII

The alkene portion of the formula LI* compound is reacted with a hypohalous acid (generated in situ from an N-Halosuccinimide in aqueous acetone containing a catalytic amount of $HClO_4$) to give a mixture of halohydrins, i.e., LII and the compound of the formula

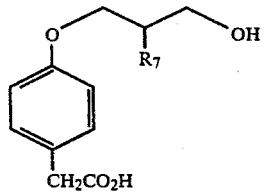

LII'

*J. M. van der Zanden & G. de Vrier, Rec. Trav. Chim., 71, p 879 (1952).

LII→LIII

The bromohydrins (LII and LII') are thereafter converted under basic conditions to the epoxide (LIII). As a base, an alkali metal (Na, K, etc.) hydroxide may be utilized. Suitable solvents for the reaction include ethers, such as, dioxane or tetrahydrofuran and alcohols ($C_1$ to $C_4$) e.g., methanol, ethanol, etc. The reaction can be run at from about 0° C. to 40° C. with room temperature as preferred.

LI→LIV

The acid portion of the compound of formula LI is esterified by treatment of LI with an excess of an alkylating agent, $CH_3$-Halo, e.g., $CH_3I$, $CH_3Br$, in the presence of an alkali metal (Na, K) carbonate in a solvent, such as, acetone, dimethylformamide, dimethylsulfoxide or hexamethylphosphoramide to give the ester of formula LIV. The reaction temperature is not critical but about room temperature is preferred for its ease.

LIII→LV

The acid portion of the epoxide (LIII) may also be esterified by using diazomethane in the presence of a solvent such as ethers (tetrahydrofuran) or a $C_1$ to $C_4$ alcohol. As above, this reaction is preferably run at room temperature.

LIV→LV

The alkene portion of the compound of formula LIV is thereafter reacted with an aromatic or aliphatic peracid, such as, m-chloroperbenzoic acid, peracetic acid, performic acid, trifluoroperacetic acid, permaleic acid, perbenzoic acid, monoperphthalic acid, o-sulfoperbenzoic acid or p-nitroperbenzoic acid. The reaction utilizes as a solvent any inert halogenated aliphatic hydrocarbon, such as, methylene chloride or chloroform. The reaction temperature may range from about 0° C. to reflux with room temperature as preferred.

LV→LVI

The epoxide portion of the compound of formula LV is thereafter reacted with a primary amine of the formula $NH_2R_1$, wherein $R_1$ is as above, in a suitable solvent, such as, $C_1$ to $C_4$ alcohols or ethers, such as, dioxane or tetrahydrofuran. The reaction temperature may vary from about 0° C. to room temperature with room temperature as preferred.

LVI→LVII

The ester portion of LVI is thereafter condensed with a primary amine of the formula

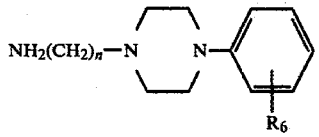

wherein n and $R_6$ are as above, to form the amide. No solvent is necessary for this step. The reaction temperature may be from about 100° C. to 150° C. with a preferred range of from about 140° C. to 145° C.

XVI→LXII

The phenol portion of XVI undergoes an O-alkylation with an epihalohydrin, e.g., epichlorohydrin, using as a base, an alkali metal hydroxide, e.g. KOH or NaOH in a mixture of $H_2O$ and dioxane, tetrahydrofuran or dimethylsulfoxide. The reaction may be carried out from about 0° C. to 100° C. with about room temperature as preferred.

LXII→LXIII

The epoxide portion of LXII is thereafter reacted with an amine of the formula $NH_2R_1$ wherein $R_1$ is as above, in an solvent, such as, a $C_1$ to $C_4$ alcohol, or an ether, such as, tetrahydrofuran or dioxane. The reaction temperature may range from about 0° C. to reflux with a range of about room temperature to 65° C. as preferred.

LXIII→LXIV

The benzyloxy portion of the compound of formula LXIII is converted to the phenol function by utilizing the reagents and reaction parameters previously disclosed for the isomer, see, step XXXVI→XXXVII.

LXIV→XXV'

The phenol portion of LXIV is reacted with a phenylpiperazine as previously disclosed in step XXXVII→XXV along with the reagents and reaction parameters.

4-(2-bromoethoxy)phenol*→LVIII

The phenol portion of the bromoethoxy phenol undergoes an O-alkylation with an alkylating agent, such as, allyl halide, e.g. chloride or bromide, in the presence of an alkali metal (Na,K) carbonate in refluxing solvent, such as, acetone. The reaction temperature should be about or at reflux of the solvent.
*F. S. H. Head, J. Chem. Soc. (C), 871 (1971)

LVIII→LIX and LIX'

The alkene portion of the compound of formula LVIII is thereafter converted to the halohydrins of formulas LIX and LIX' by utilizing the reagents and reaction parameters set forth in step LI→LII.

LIX and LIX'→LX

The halohydrins (LIX and LIX') are thereafter converted to the epoxide of formula LX by utilizing the reagents and reaction parameters set forth in step LII→LIII.

LX→LXI

The epoxide (LX) is thereafter reacted with a primary amine of the formula $NH_2-R_1$ wherein $R_1$ is as above, to give the aminoalcohol (LXI). Suitable solvents include $C_1$ to $C_4$ alcohols, ethers such as tetrahydrofuran, dimethylsulfoxide or dimethylformamide. The reaction may be carried out from about room temperature to 60° C. with a range of about room temperature to 55° C. as preferred.

LXI→XXV'

The halogen portion of LXI is thereafter displaced with a secondary amine of the formula

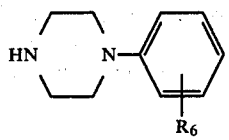

wherein $R_6$ is as above to produce a compound of formula XXV'. Solvents suitable for this reaction include $C_1$ to $C_4$ alcohols and ethers, such as, dioxane and tetrahydrofuran. The reaction may be carried out at from about 0° C. to 100° C. with 80° C. to 100° C. as preferred.

LXV*→LXVI

A compound of the formula LXV is reacted with an appropriately substituted amine of the formula

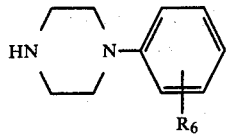

wherein $R_6$ is as above in a $C_1$ to $C_4$ alcohol. The temperature of the reaction may be varied from room temperature to the boiling point of the selected alcohol. A preferred alcohol is ethanol and the preferred reaction temperature is its boiling point.
* T. Kunitake & S. Shinkai, J. Amer. Chem. Soc., 93, 4247 (1971)

LXVI→LXVII

The compound of formula LXVI is thereafter converted to a compound of formula LXVII by treatment with a base such as an alkali or alkaline earth metal hydroxide (NaOH, KOH, Ba(OH$_2$)) in a solvent such as water, $C_1$ to $C_4$ alcohols or dimethylformamide or alkali metal (K,Na) salts or lower alcohols in solvents such as dimethylformamide or $C_1$ to $C_4$ alcohols. To this reaction mixture containing the salt of LXVI is added epihalohydrin to generate LXVII.

LXVII→LXVIII

The compound of formula LXVII is treated with an amine of the formula $$R_1NH_2$$

wherein $R_1$ is as above in a suitable solvent, e.g., $C_1$ to $C_4$ alcohols. The reaction may be carried out at from about room temperature to reflux with about reflux as preferred. A preferred solvent would be methanol. If faster reaction rates are desired, the reaction mixture can be heated above its boiling point in a pressurized vessel.

LXIX→LXVIII→LXX

The compound of formula LXVIII can alternatively be prepared from LXIX by treatment with a propenoyl halide in an inert solvent e.g., dioxane, dimethylsulfoxide, etc. at from about 0° C. to 50° C. The intermediate is treated in situ with an appropriately substituted amine of the formula

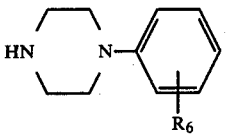

wherein $R_6$ is as above The reaction conditions are as in step LXV→LXVI above. The compound of formula LXX is generated by mixing maleic acid with LXVIII in an inert solvent.

LXXI→LXXII

The haloalkanoyl halide of formula LXXI is reacted with 4-aminophenol in the presence of excess 4-aminophenol or an equivalent of a tertiary amine, such as, pyridine, triethylamine or the like in an inert solvent, such as, an ether, e.g., tetrahydrofuran or dioxane or a polyhalogenated hydrocarbon, e.g., methylene chloride at a temperature of from about 0° C. to 100° C. A preferred reaction system for this conversion is dioxane in the presence of excess 4-aminophenol at room temperature.

LXXII→LXXIII

The compound of formula LXXII is reacted with an appropriately substituted amine of the formula

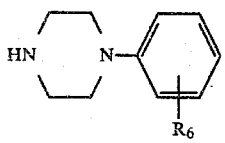

wherein $R_6$ is as above in the presence of a hydrogen halide scavenger, such as excess reagent or a less reactive amine such as triethylamine or pyridine in an inert solvent e.g., $C_1$ to $C_4$ alcohol. The reaction temperature may vary from about room temperature to 100° C.

LXXIII→LXXIV→LXXV

Conversion of the compound of formula LXXIII into that of formula LXXV is the same for reagents and reaction parameters as previously disclosed in steps LXVI→LXVII→LXVIII→LXX.

The end compounds of the subject invention may be converted to their pharmaceutically acceptable salts which exhibit comparable pharmacological activity. The end products have three amine functions, but only two of these groups are sufficiently basic to form stable salts. Accordingly they form diacid salts with various organic and inorganic acids. Some of the useful organic or inorganic acids include maleic acid, fumaric acid, tartaric acid, citric acid, hydrochloric acid, hydrobromic acid and sulfuric acid. A typical preparation of one of these salts entails the mixture of a solution of the base end product, for example, XXV in a $C_1$ to $C_4$ alcohol with a solution of a pharmaceutically acceptable acid as outlined above, also in a $C_1$ to $C_4$ alcohol. The salt thus formed crystallizes spontaneously from solution or does so on the addition of a suitable co-solvent, for example, ethyl acetate, ether, acetone, or halogenated hydrocarbons, such as, chloroform, 1,2-dichloroethane, etc.

An alternative method which may be useful in the case of compounds, such as the end product L, comprises the treatment of two parts of the base with an excess of hydrochloric acid in methanol. The solvent is then removed in vacuo to drive off the excess acid which gives the unstable trihydrochloride salt. The salt is then redissolved in methanol and one part of free base added to the solution. The dihydrochloride salt is then precipitated from solution on the addition of a co-solvent, such as disclosed above.

Preferred among the compounds disclosed herein are those of the formula

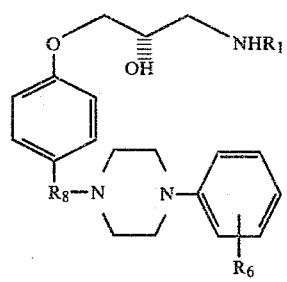

wherein $R_1$ is selected from the group consisting of lower alkyl; $R_8$ is selected from the group consisting of $-O-(CH_2)_n-$ wherein n is 2 to 20, $$-NHC-(CH_2)_n- \text{ and } -CH_2-CNH-(CH_2)_n-;$$
$$\phantom{-NHC-}\|\phantom{(CH_2)_n-\text{ and }-CH_2-C}\|$$
$$\phantom{-NHC-}O\phantom{(CH_2)_n-\text{ and }-CH_2-C}O$$

and $R_6$ is selected from the group consisting of hydrogen or lower alkoxy, the racemates thereof and pharmaceutically acceptable salts thereof. Especially preferred are those compounds wherein $R_1$ is a branched chain alkyl, such as, isopropyl or tertiary butyl, $R_8$ is the group $-O-(CH_2)_n-$ or $$-CH_2CNH(CH_2)_n-$$
$$\phantom{-CH_2C}\|$$
$$\phantom{-CH_2C}O$$

wherein n is 2 to 10, most preferably 2, and $R_6$ is hydrogen.

The compounds of the present invention and their pharmaceutically acceptable salts are useful as $\alpha$ and $\beta$ adrenergic blocking agents when utilized particularly in oral preparations. As contemplated by this invention the novel end products of the present invention and their pharmaceutically acceptable salts can be embodied in pharmaceutical dosage formulations containing from about 0.1 to about 50 mgs., most preferably 1–50 mg. with dosage adjusted to animal species and individual requirements. The novel end products and their pharmaceutically acceptable salts can be administered internally, for example, parenterally or enterally, in conventional pharmaceutical dosage forms. For example, they can be incorporated in conventional pharmaceutical dosage forms. For example, they can be incorporated in conventional liquid or solid vehicles such as water, gelatin, starch, magnesium stearate, talc, vegetable oils and the like to provide tablets, elixirs, capsules, solutions, emulsions and the like according to acceptable pharmaceutical practices. Although less preferred intravenous and intramuscular delivery systems may be utilized to provide the above novel compounds.

The disclosed compounds are in the general class of 1-aryloxy-3-alkylaminopropan-2-ols, many examples of which have been shown to possess $\beta$-adrenergic blocking activity. Since the class of compounds has an asymmetric center there are two enantiomeric forms. It has been found that the $\beta$-blocking activity of such compounds is to a large extent found in the isomer having the S-absolute configuration i.e. that isomer that is stereochemically equivalent to the naturally occurring $\beta$-agonist (R)-(−) epinephrine, whereas the racemic form exhibits approximately half of this activity, see, for example, (1) R. Howe & B. S. Rao J. Med. Chem. 11, 1118, (1968)

(2) B. Ablad et al Acta. Pharmacol Toxicol. 25, 85 (1967)

(3) L. Almirante & W. Murmann, J. Med. Chem. 9 650 (1966)

(4) M. Dukes & L. H. Smith J. Med. Chem. 14 326 (1971)

(5) J. C. Danilewicz & J. E. G. Kemp 16, J. Med. Chem., 168, (1973)

The desired S-isomer of the disclosed compounds are available in two ways:

(a) by resolution of the racemic material via a fractional crystallization of its diasterisomeric salts formed with an optically active acid, such as tartaric acid.

(b) by asymmetric synthesis using an optically active synthon of the appropriate absolute configuration. Two such synthons, IX and XV, which are readily available from D-mannitol, a naturally occurring sugar, have been used to construct the oxypropanolamine side chain in the disclosed compounds. Synthon IX is restricted to the syntheses of $\alpha$, $\beta$-blockers, wherein the functionality of the final compound is compatable with the conditions required to remove the amine protecting group, $R_3$ i.e. reductive cleavage using a mixed metal hydride. When the functionality of the final compound is not compatable with these conditions, e.g. the amido group in compound L, the synthon XV is used to incorporate the oxypropanolamine side chain.

Applicants, in setting forth the disclosure of the above specification have cited the teaching of various articles and U.S. Patents. Such citations are meant to incorporate the teachings of these references for completeness of disclosure.

The following examples are illustrative but not limitative of the present invention. All temperatures are stated in degrees Centigrade unless otherwise indicated.

EXAMPLE 1

(2R,3R,4R,5R)-Mannitol-1,2;5,6-diacetonide

A mixture of 546 g powdered D-Mannitol (3.0 mol), p-toluenesulfonic acid (3.0 g) and 780 g dimethoxypropane (7.5 mol) in 900 ml dry DMSO was stirred at ambient temperature under anhydrous conditions. Within 30 min–1 hr, all the mannitol had dissolved. After 16 hours the reaction was poured into 900 ml saturated NaHCO$_3$ solution and then was diluted further with 2 liters H$_2$O. The mixture was extracted with EtOAc (1×4.5 l; 3×3 l) and the extracts were washed in turn with H$_2$O (3×1.5 l). The combined dried (Na$_2$CO$_3$) EtOAc layers were concentrated in vacuo (bath temp ~45°) until the residue had solidified. The residue was then heated to reflux to redissolve the solids and the solution was diluted with ~8 liters of hot hexane. The mixture was allowed to cool slowly overnight and the resulting crystalline material was filtered off and washed with an ether-hexane mixture (1:3; 4×500 ml) to give (2R,3R,4R,5R)-Mannitol-1,2;5,6-diacetonide, mp 115°–119°.

The mother liquors were concentrated to dryness. A solution of the resulting residue in ether (300 ml) was diluted with about 1.6 liters of hexane. This yielded additional diacetonide, mp 119°–120°.

EXAMPLE 2

(2S)-3-Isopropylamino-1,2-propanediol acetonide from (2R,3R,4R,5R)-Mannitol-1,2;5,6-diacetonide via the imine Pb(OAc)$_4$ (263 g, 0.59 mol) was dispersed in 1500 ml dry benzene under argon. To the rapidly stirred mixture 140 g of the diacetonide was added in 5–10 g portions over 15 minutes and then further 1 g portions of diacetonide were added until the reaction gave a negative test for oxidant (KI-starch paper). A total of 150 g of acetonide (140 g+10×1 g) was used. The mixture was filtered through Celite and the filter cake was washed with 2×100 ml portions of dry benzene. The filtrate was stirred with 300 g anhydrous K$_2$CO$_3$ for 30 minutes to neutralize HOAc which was produced in the oxidation. After a second filtration through Celite, the solution was treated with 450 ml isopropylamine and 300 gr of K$_2$CO$_3$. After stirring for 30 min., the mixture was filtered and the filtrate was hydrogenated over 15 g 10% Pd/C (1 atmos; 23°). The reaction essentially stopped after the uptake of 26.4 liters of H$_2$. The catalyst was removed by filtration and concentration of the filtrate furnished the amine.

EXAMPLE 3

(2S)-3-Mesylisopropylamino-1,2-propanediol acetonide 90 ml (1.2 mol) mesyl chloride was added with stirring to a previously chilled (−10°) solution of (2S)-3-isopropylamino-1,2-propanediol acetonide (188 g; 1.087 mol) and triethylamine (288 ml; 1.63 mol) in dry THF at such a rate that the reaction temp did not exceed 5°. Reaction was then stirred at 10°–15° for 30 min whereupon it was diluted with 1.5 l brine. The layers were separated and the aqueous layers were extracted with ether (3×500 ml). The organic layers were washed in turn with brine (2×500 ml) and then were combined, dried (Na$_2$SO$_4$), and evaporated to give the N-mesylate as an oil.

A small portion was recrystallized (3×) from hexane to give analytically pure material, mp 33°–34°; $[\alpha]_D^{25}$ −14.76° (c, 1.0, CHCl$_3$).

Anal. Calcd. for C$_{10}$H$_{21}$NO$_4$S: C, 47.79; H, 8.42; N, 5.57; S, 12.76. Found: C, 47.87; H, 8.66; N, 5.72; S, 12.89.

EXAMPLE 4

(2S)-3-N-Mesylisopropylamino-1,2-propanediol 200 ml of prewashed (H$_2$O and MeOH) Dowex 50W-8X ion exchange resin (H+ form) was added to a solution of 264 g crude (2S)-3-N-mesylisopropylamino-1,2-propanediol acetonide in methanol (1 liter) and water (325 ml). The mixture was stirred under reflux for 90 min. The cooled mixture was filtered and the filtrate for concentrated in vacuo. The residue was evaporated several times from benzene-EtOH mixtures to remove the last traces of water. The resulting solid was triturated with 2.5 l ether to give the diol, mp 67°–70°. Concentration of the ether furnished additional diol, mp 64°–66°. Crystallization from ethyl acetate-hexane furnished the analytically pure material, mp 73°–74°; $[\alpha]_D^{25}$ −15.94° (c, 1.0, H$_2$O).

Anal. Calcd. for C$_7$H$_{17}$NO$_4$S: C, 39.79; H, 8.11; N, 6.63; S, 15.18. Found: C, 39.83; H, 8.40; N, 6.66; S, 14.96.

EXAMPLE 5

(S)-1-Mesyloxy-2-hydroxy-3-N-mesylisopropylaminopropane 19.1 g (90.5 mmol) N-mesyl-1,2-dihydroxy-3-isopropylaminopropane was dissolved in 150 ml anhydrous pyridine under argon and cooled to −45°. 7.0 ml (90.4 mmol) mesyl chloride was added dropwise over 5 minutes and the mixture was stirred at −45° for 5 hours. The cold mixture was then diluted with 100 ml H$_2$O followed by 200 ml 6 N HCl and extracted with EtOAc (3×). The EtOAc layers were washed in turn with 3 N HCl (1×250 ml), brine (2×) and NaHCO$_3$ solution (1×). The combined extracts were combined and evaporated to give the O,N-dimesylate an an oil which solidified on standing.

This material was contaminated with ~2% trimesylate. A small sample was purified in the following way: 500 mg was dissolved in 10 ml water and filtered free of any undissolved trimesylate. The filtrate was extracted with ether (2×) and with EtOAc (2×). The EtOAc layers were combined, dried (Na$_2$SO$_4$), and evaporated. Crystallization of the residue from ether furnished the analytical sample, mp 51°-52°, $[\alpha]_D^{25} - 1.21°$ (c, 1.0, H$_2$O).

Anal. Calcd. for C$_8$H$_{19}$NO$_6$S$_2$: C, 33.21; H, 6.59; N, 4.84; S, 22.16. Found: C, 33.33; H, 6.13; N, 4.76; S, 22.18.

EXAMPLE 6

(S)-1-Tosyloxy-2-hydroxy-3-N-mesylisopropylaminopropane

A stirred solution of 63.3 g (0.3 mol) diol of Example 4 in 450 ml pyridine was cooled to −20° and 85.5 g tosyl chloride (0.45 mol) was added. The reaction mixture was stirred in an ice-water bath for 2 hr whereupon 5-10 g ice was added to the mixture and the stirring was continued for an additional 15 minutes before it was poured into a mixture of ice (1 kg) and concentrated HCl (500 ml) and extracted with CH$_2$Cl$_2$ (1×1 l; 2×500 ml). The extracts were washed in turn with brine (1× 500 ml) and 5% NaHCO$_3$ solution. The combined, dried (Na$_2$SO$_4$) extracts were concentrated in vacuo to give the mono-tosylate as an oil. A small portion was purified for analysis by chromatography; $[\alpha]_D^{25} + 5.65°$ (c, 1.0, CHCl$_3$).

Anal. Calcd. for C$_{14}$H$_{23}$NO$_6$S$_2$: C, 46.01; H, 6.34; N, 3.83; S, 17.55. Found: C, 46.11; H, 6.53; N, 3.67; S, 16.97.

EXAMPLE 7

(2S)-1-Chloro-2-hydroxy-3-N-mesylisopropylaminopropane

A mixture of 10.55 g (50 mmol) of diol of Example 4, 9.0 g (75 mmol) of trimethylorthoacetate and 0.4 g (3.27 mmol) of benzoic acid was heated with stirring at 80° for 45 min. The viscous reaction mixture was cooled and partioned between CH$_2$Cl$_2$ and saturated NaHCO$_3$ solution. The CH$_2$Cl$_2$ layer was dried (Na$_2$SO$_4$) and evaporated to give 14.5 g of the crude orthoacetate which was then dissolved in 75 ml dry CH$_2$Cl$_2$ and treated with 12 ml (95 mmol) trimethylchlorosilane and heated at reflux for 60 minutes. The solvent was removed in vacuo and the residue was dissolved in 100 ml 0.3 N methanolic HCl and the mixture was left at ambient temperature for ~65 hrs. The solvent was removed under reduced pressure and the residual oil was chromatographed over silica gel (50 g) to give the pure chlorohydrin as an oil, $[\alpha]_D^{25} - 12.7°$ (c, 1.0 MeOH).

Anal. Calcd. for C$_7$H$_{16}$ClNO$_3$S: C, 36.60; H, 7.02; N, 6.10; Cl, 15.43; S, 13.96. Found: C, 36.38; H, 7.32; N, 5.98; Cl, 15.15; S, 13.53.

EXAMPLE 8

(2S)-3-Benzyloxypropandiol, 1,2-acetonide 44 g of a 50% dispersion of NaH in oil was placed in a flask and washed with dry hexane. To the flask was then charged a solution of 120 g benzyl chloride in 1500 ml dry DMF. To this stirred mixture, a solution of (2S)-glycerol-2,3-acetonide (120 g) in dry DMF (500 ml) was added over 45 min at ambient temperature (initial reaction temperature was 17° and it rose to a maximum of 27° during the addition). Stirring was continued for 1 hr after the addition was completed and then MeOH (~30 ml) was added dropwise to destroy excess hydride. The system was then equipped for distillation and the DMF was distilled off in vacuo (~55°-60°; water aspirator). The residue was diluted with brine (2 liters) and extracted with CH$_2$Cl$_2$ (3×1 liter). The organic layers were washed in turn with brine and then were combined, dried (MgSO$_4$) and evaporated to give an oil.

The oil was distilled in vacuo to give the benzyl ether (bp 78°-80°, 0.05 mm).

EXAMPLE 9

(2R)-3-Benzyloxy-1,2-propanediol

A suspension of 75 ml Dowex 50-8x (H$^+$ form) in a stirred solution of 254.6 g (1.15 mol) (2S)-3-benzyloxypropanediol, acetonide in 800 ml MeOH and 200 ml H$_2$O was heated at reflux for 1 hr. The resin was filtered off and the filtrate was concentrated in vacuo. The diol was freed from residual H$_2$O by evaporating it several times from ethanol-benzene mixtures to give it as a colorless oil.

EXAMPLE 10

2(R,S),4(S)-2-Methoxy-2-methyl-4[(benzyloxy)methyl)]-1,3-dioxolane

A stirred solution of 207 g (1.13 mol) (2R)-3-benzyloxy-1,2-propanediol in 200 g (1.66 mol) trimethylorthoacetate containing 3 g (0.024 mol) was heated in an oil bath at 75° in a flask fitted for downward distillation. Methanol thus was removed from the reaction as it was formed. After 40 min the reaction mixture was cooled and partitioned between CH$_2$Cl$_2$ (800 ml) and 1 N NaOH solution (200 ml). The aqueous phase was extracted further with CH$_2$Cl$_2$ (2×250 ml) and then the organic layers were washed in turn with 200 ml. 0.5 N NaOH solution. The combined CH$_2$Cl$_2$ layers were dried (Na$_2$SO$_4$) and concentrated to dryness to give the cyclic orthoacetate as a colorless oil.

Analysis of its nmr spectrum showed it to be a 4:3 mixture of diastereoisomers. A small sample was distilled (~165°/0.1 mm) to give the analytical sample $[\alpha]_D^{25} + 7.4°$ (c, 1.0, MeOH).

Anal. Calcd. for C$_{13}$H$_{18}$O$_4$: C, 65.53; H, 7.61. Found: C, 65.84; H, 7.76.

EXAMPLE 11

(2S)-3-Benzyloxy-2-acetoxy-1-chloropropane 155 ml (1.21 mol) trimethylchlorosilane was added to a solution of 270 g (1.13 mol) crude cyclic orthoacetate in 600 ml dry $CH_2Cl_2$ and the mixture was heated at reflux in an inert atmosphere for 30 minutes. The solvent and excess reagent were removed under reduced pressure to give the crude chloroacetate as a mobile oil. This material was used without further purification.

A small portion was distilled ($\sim 165°/0.1$ mm) to give the analytical sample $[\alpha]_D^{25} + 10.8°$ (c, 1.0, MeOH).

Anal. Calcd. for $C_{12}H_{15}ClO_3$: C, 59.39; H, 6.23: Cl, 14.61. Found: C, 59.50; H, 6.31; Cl, 14.35.

EXAMPLE 12

(2S)-1,2-Epoxy-3-benzyloxypropane

A chilled solution of 115 g NaOH (2.875 mol) in 600 ml $H_2O$ was added dropwise over 20 minutes to a cooled solution of the crude chloroacetate of Example 11 (theory 1.13 mol) in MeOH (800 mol) with stirring. The reaction temperature was maintained at <12° during the addition. After stirring an additional 1 hr at $\sim 12°$, the reaction was cooled to 5° and then neutralized to pH 7.0 using dilute $H_2SO_4$. The reaction was then concentrated in vacuo (bath temp. $\sim 25°$) to remove MeOH and then it was diluted with 250 ml brine and extracted with $CH_2Cl_2$ ($1 \times 750$ ml; $1 \times 400$ ml). The $CH_2Cl_2$ extracts were combined, dried ($Na_2SO_4$) and evaporated to dryness. The resulting oil was distilled in vacuo to give the epoxide, bp 84°–86°/0.45 mm; $[\alpha]_D^{25} - 10.64°$ (c, 1.0 MeOH).

Anal. Calcd. for $C_{10}H_{12}O_2$: C, 73.15; H, 7.27. Found: C, 73.21; H, 7.51.

EXAMPLE 13

(S)-1-(4-Benzyloxyphenoxy)-2-hydroxy-3-N-mesylisopropylaminopropane

Method A—Condensation of the product of Example 6 with benzyloxyphenol

A solution of (S)-1-tosyloxy-2-hydroxy-3-N-mesylisopropylaminopropane (103 g, 0.282 mol) and p-benzyloxyphenol (79 g, 0.395 mol) in 500 ml DMSO was treated with 93.7 ml 4 N NaOH (0.375 mol) and stirred at 100° under argon for 2½ hr. The solution was cooled and 300 ml 1 N NaOH was added slowly to the vigorously stirred solution followed by 600 ml $H_2O$. The resulting solid was removed by filtration and was washed with water. After partial air drying, the solid was dissolved in $CH_2Cl_2$ and the solution was dried over $MgSO_4$. The decolorized (charcoal) solution was evaporated to dryness and the resulting solid residue was triturated with hot ether (1.5 liters). Filtration of the colorless solid gave the end product, mp 91°–93°.

Recrystallization from $CH_2Cl_2$-ether gave the pure sample, mp 94°–95°; $[\alpha]_D^{25} - 0.93°$ (c, 1.0, $CHCl_3$).

Anal. Calcd. for $C_{20}H_{27}NO_5S$: C, 61.04; H, 6.91; N, 3.56. Found: C, 61.04; H, 6.90; N, 3.43.

EXAMPLE 14

Method B—Condensation of the product of Example 7 with benzyloxyphenol to give product of Example 13

A solution of 8.3 g (36.1 mmol) of (2S)-1-chloro-2-hydroxy-3-N-mesylisopropylaminopropane and 8.69 g (43.4 mmol) of p-benzyloxyphenol in 75 ml DMSO was treated with 10.86 ml 4 N NaOH (43.4 mmol) and the mixture was heated at 100° for 5 hours. To the cooled reaction mixture 40 ml 1 N NaOH and 60 ml $H_2O$ were added with stirring and the resulting solid was collected by filtration and was washed well with $H_2O$. The dried crude product was recrystallized from EtOAc-hexane to yield the end product as white needles, mp 93°–94°.

EXAMPLE 15

(S)-1-(4-Hydroxyphenoxy)-2-hydroxy-3-N-mesylisopropylaminopropane

A slurry of 10% Pd/C in 30 ml EtOAc was added to a solution of 38.4 g (S)-1-(4-benzyloxyphenoxy)-2-hydroxy-3-N-mesylisopropylaminopropane in 850 ml MeOH and the mixture was hydrogenated (760 mm; 20°). Within 1 hr the uptake of $H_2$ stopped (total 2.6 liters) and the catalyst was removed by filtration through Celite. The filtrate was concentrated under reduced pressure and the residue was crystallized from $CH_2Cl_2$-ether to give the phenol, mp 91°–93°. Recrystallization of a sample from EtOAc-hexane gave the analytically pure material, mp 92°–94°; $[\alpha] - 1.93°$ (c, 1.0, $CHCl_3$).

Anal. Calcd. for $C_{13}H_{21}NO_5S$: C, 51.47; H, 6.98; N, 4.62; S, 10.57. Found: C, 51.38; H, 6.89; N, 4.58; S, 10.46.

EXAMPLE 16

(S)-4-(2-Hydroxy-3-N-mesylisopropylaminopropoxy)-phenoxyacetic acid

To a stirred solution of a 24 g (0.08 mol) of (S)-1-(4-hydroxyphenoxy)-2-hydroxy-3-N-mesylisopropylaminopropane in 240 ml of absolute ethanol (argon atmosphere) was added at room temperature 9.04 g (0.08 mol) of potassium t-butoxide. After stirring for 15 min, 13.36 g (0.08 mol) of ethyl bromoacetate was added and the reaction mixture was heated under reflux overnight. It was then cooled and concentrated in vacuo. The residue was acidified to pH 2 with 1 N HCl, and was then dissolved in EtOAc. The organic layer was then washed twice with 1 N NaOH, once with $H_2O$ and dried ($Na_2SO_4$). Evaporation of the solvent gave the crude ester as an oil which solidified on standing.

To a solution of 29 g (0.75 mol) of crude ester in 290 ml of MeOH, was added 40 ml of 4 N NaOH solution. The reaction mixture was refluxed for ten minutes and then allowed to cool to room temperature for one hour. Most of the solvent was evaporated in vacuo and the residue treated with 50 ml of 6 N HCl solution. The resulting solid was collected by filtration and crystallized twice from acetone-hexane to yield the end product, mp 128°–129°. Crystallization from acetone-hexane gave the analytical sample, mp 129°–130°; $[\alpha]_D^{25} + 1.5°$ (c, 1.0, $CH_3OH$).

Anal. Calcd. for $C_{15}H_{23}NO_7S$: C, 49.85; H, 6.41; S, 8.87; N, 3.87. Found: C, 49.84; H, 6.58; S, 8.83; N, 3.80.

EXAMPLE 17

1-(2-Chloroethyl)-4-phenylpiperazine

To a stirred solution of N-phenylpiperazine (95% pure; 300 g; 1.85 mol) in 1 l MeOH previously chilled to $-20°$ was added in one portion a chilled solution of ethylene oxide (150 ml) in MeOH (250 ml). The mixture was stirred in an ice-water bath overnight. After the solvent and excess reagent were removed in vacuo, the residue was taken up in toluene and re-evaporated to remove residual MeOH.

The crude 1-(2-hydroxyethyl)-4-phenylpiperazine ($\sim 400$ g) thus obtained was dissolved in dry $CH_2Cl_2$ (3.5 l) containing triethylamine (400 ml; 2.9 mol) and the solution was cooled to $-10°$. A solution of 250 g (2.18 mol) mesyl chloride in 300 ml CH$_2$Cl$_2$ was added to the stirred mixture over 30 min and then the reaction was allowed to warm up to room temp. It was then stirred at ambient temperature until the in situ conversion of the intermediate mesylate to the chloro compound was completed (16-40 hrs). Water (1 l) was added and the layers separated. The aqueous layer was washed with CH$_2$Cl$_2$ (1×300 ml) and then the combined CH$_2$Cl$_2$ phases were dried (K$_2$CO$_3$) and evaporated. The residue was triturated with hot hexane (1×1 l; 4×200 ml) and the combined extracts were decolorized (charcoal) and then cooled to 0°-5°. Filtration of the resulting colorless crystals afforded 1-(2-chloroethyl)-4-phenylpiperazine, mp 56°-58°. Concentration of the mother liquor to ~400 ml furnished additional product, mp 55°-57°.

Recrystallization of a small sample from hexane furnished the analytically pure material, mp 59°-60°.

Anal. Calcd. for C$_{12}$H$_{17}$ClN$_2$: C, 64.13; H, 7.62; N, 12.47; Cl, 15.78. Found: C, 64.30; H, 7.61; N, 12.41; Cl, 15.57.

EXAMPLE 18

1-(2-Chloroethyl)-4-(2-methoxyphenyl)-piperazine

In a procedure, analogous to the one described above, 50 mmol of N-(2-methoxyphenyl)piperazine was converted to 1-(2-chloroethyl)-4-(2-methoxyphenyl)-piperazine, mp 36.5°-37°.

Anal. Calcd. for C$_{13}$H$_{19}$ClN$_2$O: C, 61.29; H, 7.52; N, 10.99; Cl, 13.92. Found: C, 61.22; H, 7.52; N, 11.02; Cl, 13.93.

EXAMPLE 19

1-[2-(4-Benzyloxyphenoxy)ethyl]-4-phenylpiperazine 26.25 ml 4 N NaOH (0.105 mol) was added to a stirred mixture of 21.0 g (0.105 mol) 4-benzyloxyphenol and 22.5 g (0.1 mol) of 1-(2-chloroethyl)-4-phenylpiperazine in 250 ml DMSO and the reaction was heated at 60° for 60 min. After cooling, the stirred mixture was diluted with 50 ml 1 N NaOH solution and the resulting crystalline precipitate was collected by filtration and washed with water to give, after drying in vacuo, essentially pure end product, mp 116°-119°.

A small sample was recrystallized from ethyl acetate for analysis, mp 120°-121°.

Anal. Calcd. for C$_{25}$H$_{28}$N$_2$O$_2$: C, 77.29; H, 7.26; N, 7.21. Found: C, 77.19; H, 7.08; N, 7.12.

EXAMPLE 20

1-[2-(4-Hydroxyphenoxy)ethyl]-4-phenylpiperazine

Method A—By HCl cleavage of the benzyl ether of Example 19

35.75 g of 1-[2-(-4-benzyloxyphenoxy)ethyl]-4-phenylpiperazine was added rapidly with stirring to 75 ml concentrated HCl and the mixture was heated on a steam bath for 15 minutes. During this time starting material dissolved and then a white crystalline solid began to form and eventually the reaction mixture almost solidified. The reaction was cooled to ~5° and then was diluted with 100 ml EtOH. The solids were filtered off and were washed in EtOH and ether to give 1-[2-(4-hydroxyphenoxy)ethyl]-4-phenylpiperazine as its monohydrochloride. The salt was dissolved in 150 ml hot MeOH and 50 ml H$_2$O and was then treated with 25 ml triethylamine. Water was then added to the refluxing mixture just to the cloud point whereupon the product began to crystallize from solution. The mixture was chilled and the solids were collected by filtration to give the end product, mp 142°-143°.

The analytically pure material, 143°-144°, was obtained by recrystallization from EtOAc.

Anal. Calcd. for C$_{18}$H$_{22}$H$_2$O: C, 72.46; H, 7.43; N, 9.39. Found: C, 72.32; H, 7.23; N, 9.25.

EXAMPLE 21

Method B—Hydrogenolysis of benzyl group in the product of Example 19 to produce the end product of Example 20

1-(4-Benzyloxyphenoxy)-4-phenylpiperazine (211.2 g; 0.544 mol) in 1 l HOAc was hydrogenolyzed over 20 g of 10% Pd/C (21°; 1 atoms). The absorption of H$_2$ essentially stopped after 3 hr (total uptake 15.1 l). The catalyst was filtered off through Celite and the filtrate was concentrated to dryness in vacuo. The crude material was dissolved in 750 ml hot MeOH and 250 ml warm (~70°) H$_2$O was added followed by 120 ml of triethylamine. H$_2$O was then added to the cloud point whereupon the product started to crystallize rapidly from solution. The mixture was cooled to ~5° and the crystalline material was removed by filtration and washed with MeOH-H$_2$O (1:1) to give, the end product, mp 143°-144°.

EXAMPLE 22

(S)-1-[2-(4-(2-Hydroxy-3-N-mesylisopropylamino-propoxy)phenoxy)ethyl]-4-phenylpiperazine Method A—Condensation of the compound of Example 15 with 1-(2-chloroethyl)-4-phenylpiperazine 11.0 ml 4 N NaOH solution (44 mmol) was added to a stirred solution of 13.3 g (43.9 mmol) (S)-1-(4-hydroxyphenoxy)-2-hydroxy-3-N-mesylisopropylaminopropane and 10.0 g (44.4 mmol) 1-(2-chloroethyl)-4-phenylpiperazine in 100 ml DMSO. The mixture was heated at 60° under argon and then was cooled and diluted with 200 ml water. The resulting solid was collected by filtration, was washed with water and then was dissolved in CH$_2$Cl$_2$. The CH$_2$Cl$_2$ solution was washed with 5% Na$_2$CO$_3$ solution and then was dried (K$_2$CO$_3$) before evaporation in vacuo to a white solid. Crystallization of the product from EtOAc furnished the end product in two crops: mp 104°-106°; mp 103°-105°.

A small sample of the second crop was recrystallized from EtOAc to give the analytically pure material, mp 104°-106°; $[\alpha]_D^{25}$ −0.5° (c, 1%, CHCl$_3$).

Anal. Calcd. for C$_{25}$H$_{37}$N$_3$O$_5$S: C, 61.08; H, 7.59; N, 8.55; S, 6.52. Found: C, 61.14; H, 7.74; N, 8.40; S, 6.41.

EXAMPLE 23

Method B—Condensation of the product of Example 6 and 1-[2-(4-hydroxyphenoxy)-ethyl]-4-phenylpiperazine 300 ml 4 N NaOH (1.2 mol) was added to a stirred mixture of 362 (0.99 mol) (S)-1-tosyloxy-2-hydroxy-3-N-mesylisopropylaminopropane and 298.4 g (1 mol) 1-[2-(4-hydroxyphenoxy)ethyl]-4-phenylpiperazine in 2.4 l DMSO and the reaction was heated at 95°-100° for 12 hrs. The cooled mixture was diluted with 1 l 1 N NaOH and 7 l H$_2$O and was extracted using benzene (1×12 l; 1×2). The organic extracts were washed in turn with water (2×2 l) and then were dried (K$_2$CO$_3$) and evaporated to dryness. A solution of the residue in hot EtOAc was charcoaled and, after concentration to ~2.5 l was stored at 0°–5° overnight to give the end product of Example 22. The mother liquors were concentrated to ~500 ml and diluted with 500 ml hexane which yielded additional product. The two crops were combined and recrystallized from acetone-hexane to give essentially pure material, mp 95°–100°.

EXAMPLE 24

(S)-1-(4-Benzyloxyphenoxy)-3-benzyloxy-2-propanol 4.5 g (0.04 mol) KOC(CH$_3$)$_3$ was added to a solution of 66.3 g (0.404 mol) (S)-1,2-epoxy-3-benzyloxypropane and 97.0 g (0.484 mol) p-benzyloxyphenol in 240 ml MeOH and the mixture was heated overnight at reflux. The reaction was cooled and then was diluted with the slow addition of 1 l 1 N NaOH. The resulting solids were recovered by filtration and were washed with 0.5 N NaOH and with water and air dried. The material was dissolved in 800 ml CH$_2$Cl$_2$ and the solution was washed with H$_2$O (3×150 ml). The water layers were backwashed in turn with 200 ml CH$_2$Cl$_2$ and concentration of the combined, dried (Na$_2$SO$_4$) CH$_2$Cl$_2$ layers gave essentially pure product.

A small sample was crystallized from CH$_2$Cl$_2$-hexane (2×) to give the analytically pure material, mp 62°–63.5°; $[\alpha]_D^{25}$ +4.4° (c, 1.0, MeOH).

Anal. Calcd. for C$_{23}$H$_{24}$O$_4$: C, 75.80; H, 6.64. Found: C, 75.82; H, 6.60.

EXAMPLE 25

(S)-3-(4-Hydroxyphenoxy)-1,2-propanediol

A solution of 138 g (0.378 mol) (S)-1-(4-benzyloxyphenoxy)-3-benzyloxy-2-propanol in 1.7 liters HOAc containing 36 ml concentrated HCl was hydrogenated over 14 g 10% Pd/C at normal temp and pressure. The uptake of hydrogen essentially stopped after 70 min (~17.7 liters H$_2$ used). The catalyst was removed by filtration through Celite and concentration of the filtrate to dryness gave an oil which was then dissolved in 800 ml 0.5 N methanolic HCl and left at room temp overnight to hydrolyze the acetates which had been formed during the hydrogenation. The reaction was concentrated to dryness and the residue was evaporated several times from CH$_2$Cl$_2$ to eliminate residual HCl. Trituration of the resulting solid with ether furnished the essentially pure end product.

0.5 g was crystallized from MeOH-CHCl$_3$ to give the analytically pure material, mp 149.5°–151°; $[\alpha]_D^{25}$ +8.01° (c, 1.0, MeOH).

Anal. Calcd. For C$_9$H$_{12}$O$_4$: C, 58.69; H, 6.57. Found: C, 58.43; H, 6.73.

EXAMPLE 26

(R)-1-(4-Hydroxyphenoxy)-3-chloro-2-propanol

A stirred mixture of 62.15 g (0.337 mol) (S)-3-(4-hydroxyphenoxy)-1,2-propanediol (0.025 mol) and benzoic acid in 60 g trimethylorthoacetate was heated in an oil bath at 80°. Methanol was distilled from the system as it was formed. After 30 minutes the reaction mixture was cooled and partitioned between 750 ml benzene and 250 ml saturated NaHCO$_3$ solution. The benzene layer was washed with another 250 ml portion of NaHCO$_3$ solution and then the aqueous layers were backwashed with 250 ml benzene. The combined organic contracts were dried (Na$_2$SO$_4$) and evaporated in vacuo to give the cyclic orthoacetate as an oil. The total crude material was then dissolved in 400 ml dry CH$_2$Cl$_2$ and treated with 65 ml trimethylchlorosilane. After being heated at reflux for 30 minutes, the solution was concentrated to dryness under reduced pressure. The residue was evaporated from toluene to remove excess reagent to give crude (R)-3-(4-hydroxyphenoxy)-2-acetoxy-1-chloropropane as an oil. The acetate was hydrolyzed by heating a solution of the crude product in 250 ml 0.5 N methanolic HCl at 55° for 30 min. The solvent was concentrated in vacuo and the residue was diluted with water and was extracted with EtOAc to give the crude chlorohydrin. The crude material was dissolved in 120 ml CH$_2$Cl$_2$ and placed on a column of silica gel (800 g made up in CH$_2$Cl$_2$). Three liters of CH$_2$Cl$_2$ eluent were collected and discarded and the product was eluted using 3 liters of CH$_2$Cl$_2$EtOAc (1:1) to give after evaporation of the solvent, the end product as an oil.

EXAMPLE 27

(S)-1,2-Epoxy-3-[4-(2-(4-phenyl-1-piperazinyl)ethoxy)-phenoxy]propane 29.5 ml 4 N NaOH (0.118 mol) was added at a rapid dropwise rate to a stirring solution of 12 g (59 mmol) (R)-1-(4-hydroxyphenoxy)-3-chloro-2-propanol in 210 ml DMSO. During the addition the temp of the reaction was maintained <25° by means of a cooling bath. After the reaction had stirred at ~20° for 10 min, 12.6 g (56.3 mmol) 1-(2-chloroethyl)-4-phenylpiperazine was added in one portion and the mixture was heated at 40° for 2½ hr (after 20 min, a solid material began to crystallize from solution). The mixture was cooled and diluted with 30 ml H$_2$O. The crystalline precipitate was collected by filtration and was washed with 100 ml DMSO-H$_2$O (3:1) and with water. After air drying, the solids were dissolved in benzene (600 ml) and washed with H$_2$O (3×150 ml). The aqueous layers were backwashed with benzene (1×200 ml). The combined benzene extracts were dried (K$_2$CO$_3$) and evaporated to give the end product as a white solid.

A small sample from a previous run was filtered through a short silica gel column and crystallized from acetone to give the analytically pure material, mp 118°–119.5°; $[\alpha]_D^{25}$ −10.1° (c, 1.0, MeOH).

Anal. Calcd. for C$_{21}$H$_{26}$N$_2$O$_3$: C, 71.16; H, 7.39; N, 7.90. Found: C, 71.19; H, 7.28; N, 7.92.

EXAMPLE 28

(S)-1-(4-Benzyloxyphenoxy)-2-hydroxy-3-isopropylaminopropane

Under a flow of argon 318 ml of 70% Red-al solution was added over 15 min to a stirred solution of 36.5 g of (S)-1-(4-benzyloxyphenoxy)-2-hydroxy-3-N-mesylisopropylaminopropane in 800 ml dry benzene. After the addition was complete, the mixture was refluxed with stirring for 3 hours. The reaction was cooled using an ice-water bath and 30 ml 1 N NaOH was added dropwise to destroy excess hydride, followed by 800 ml 2 N NaOH. The phases were separated and the organic layer was washed in 1 N NaOH and with water. The aqueous phase and washings were back extracted with benzene (1×500 ml). The combined benzene extracts were dried (anhydr. K$_2$CO$_3$) and evaporated to give a solid. The crude material was dissolved in 1500 ml ether and the solution was concentrated to ~750 ml. The resulting crystalline amine was filtered off to give pure material, mp 93°–95°; $[\alpha]_D^{25}$ −6.26° (c, 1.0, CHCl$_3$).

Concentration of the mother liquors gave two additional crops of product: Crop #2, mp, 91°–93° and Crop #3, mp, 89°–93°.

Anal. Calcd. for $C_{19}H_{25}NO_3$: C, 72.35; H, 7.99; N, 4.44. Found: C, 72.38; H, 8.16; N, 4.43.

EXAMPLE 29

(S)-1-(4-Hydroxyphenoxy)-2-hydroxy-3-isopropylaminopropane

Method A—From (S)-1-(4-benzyloxyphenoxy)-2-hydroxy-3-isopropylaminopropane

A slurry of 5.4 g 10% Pd/C in 50 ml benzene was added to a solution of 54.1 g of the amine in 600 ml MeOH. The attempted hydrogenolysis of this mixture resulted in very slow uptake of hydrogen due to catalyst poisoning by minor sulfur containing impurities in the amine. The poisoned catalyst was replaced by 5.4 g fresh Pd/C and then 4.2 liters of $H_2$ was taken up within 40 minutes. The catalyst was removed by filtration and the filtrate was concentrated in vacuo. Crystallization of the residue from acetone furnished the phenol amine, mp 125°-127°; $[\alpha]_{25}{}^D$ −22.1° (C, 1.0, 0.1 N HCl). The analytically pure sample, mp 125°-127°, was crystallized from acetone.

Anal. Calcd. for $C_{12}H_{19}NO_3$: C, 63.97; H, 8.50; N, 6.22. Found: C, 63.81; H, 8.68; N, 6.40.

EXAMPLE 30

Method B—From (R)-1-(4-Hydroxyphenoxy)-3-chloro-2-propanol to produce the end product of Example 29

A solution of 50 g (0.247 mol) (R)-1-(4-hydroxyphenoxy-3-chloro-2-propanol in 300 ml methanol containing 100 ml isopropylamine was refluxed overnight. The solvent was removed in vacuo and the residue was evaporated twice from methanol to eliminate remaining isopropylamine. The crude was dissolved in 250 ml 1 N HCl and the solution was extracted with ether (2×) to remove non-basic impurities. The aqueous layer was chilled in an ice-water bath and was treated with 13.5 g $Na_2CO_3$ (0.255 equiv.). After 5 min the phenolamine began to crystallize from solution. The mixture was stirred in the ice-water bath for 30 min and then was stored at 0° for 1 hr. The product was collected by filtration and was washed with water to give the phenolamine, mp 124°-126°. 60 g of NaCl was added to the combined filtrate and washings and the resulting solution was extracted with 6×200 ml portions of EtOAc. The extracts were dried ($K_2CO_3$) and evaporated to give an additional amount of phenolamine.

Crystallization of the total product from acetone (charcoal) furnished pure phenol mp 124°-126°; $[\alpha]_D{}^{25}$ −22.0° (c, 1.0, 0.1 N HCl).

EXAMPLE 31

(S)-1-[2-(4-(2-Hydroxy-3-(1-methylethyl)amino)propoxy)phenoxy)ethyl]-4-phenylpiperazine and Its Bis-maleate Salt Method A A solution of 15.35 g (42.5 mmol) of (S)-4-(2-hydroxy-3-N-mesylisopropylaminopropoxy)phenoxyacetic acid in 170 ml of dry tetrahydrofuran was cooled (0°). To this solution (argon atmosphere) was added 5.16 g (51 mmol) of triethylamine followed by the dropwise addition of 4.61 g (42.5 mmol) of ethyl chloroformate. The reaction mixture was allowed to stir at 0° for one hr and was then filtered from the resulting precipitate. The filtrate was then treated with 10.35 g (63.8 mmol) of N-phenylpiperazine and the reaction mixture was allowed to stir under argon for 90 min at room temp. The solvent was then evaporated in vacuo and the residue was dissolved in methylene chloride and treated with 100 ml of 5 N HCl solution. The aqueous layer was extracted twice with methylene chloride. The organic layers were then washed twice with 5 N HCl solution and once with 5% $NaHCO_3$ solution. The combined organic layers were dried ($Na_2SO_4$) and evaporated to give an oil which was dissolved in benzene and chromatographed on silica gel (400 g). The column was eluted with benzene-ethyl acetate mixtures, the product being eluted with benzene-ethyl acetate (3:1) and pure ethyl acetate. Evaporation of these solvent fractions yielded the intermediate amide 1-[(S)-4-(2-hydroxy-3-N-mesylisopropylaminopropoxy)phenoxyacetyl]-4-phenylpiperazine as an oil.

To a portion of this material (18 g, 35.7 mmol) in 600 ml of dry benzene was added dropwise (over 25 min) 113 ml of 70% sodium bis(2-methoxyethoxy)-aluminum hydride in benzene (Red-al). The reaction mixture was heated under reflux for 30 min and was then cooled and treated dropwise with 120 ml of 1 N NaOH solution followed by 1 l of $H_2O$. The resulting mixture was extracted twice with 1500 ml of benzene and the organic layers were washed twice with water. The dried ($Na_2SO_4$) organic layers were concentrated in vacuo to give a colorless solid, mp 88°-95°. Crystallization from methylene chloride-ether gave the end product, mp 99°-102°. Further crystallization from the same solvent system gave the analytical sample, mp 102°-104°; $[\alpha]_D{}^{25}$ −0.3° (c, 1.0, $CH_3OH$).

Anal. Calcd. for $C_{24}H_{35}N_3O_3$: C, 69.70; H, 8.53; N, 10.16. Found: C, 69.73; H, 8.65; N, 10.00.

Method B—From (S)-1-(4-hydroxyphenoxy)-2-hydroxy-3-isopropylaminopropane 18.75 ml 4 N NaOH (75 mmol) was added to a solution of 16.0 g (71.4 mmol) 1-(2-chloroethyl)-4-phenylpiperazine and 16.8 g (75 mmol) 1-(4-hydroxyphenoxy)-2-hydroxy-3-isopropylaminopropane, 150 ml DMSO and the mixture was stirred at 60° for 3 hours. 100 ml 1 N NaOH was added slowly to the cooled solution followed by 100 ml $H_2O$ and the resulting solid was recovered by filtration and was washed well with water. The crude solid was dissolved in $CH_2Cl_2$ (600 ml) and the solution was dried ($K_2CO_3$) and evaporated to give the crude product. The material was dissolved in 400 ml hot EtOAc and diluted with 400 ml hexane and was stored overnight 0°-5°. The resulting solid was collected by filtration and was washed with 200 ml EtOAc-hexane (1:1) to give the end product, mp 102°-104°.

23.3 g (56.4 mmol) of the amine was added to a hot solution of maleic acid (13.34 g; 115 mmol) in 300 ml MeOH. Hot EtOAc was added portionwise to the refluxing solution such that the volume remained at ~500 ml until the salt began to crystallize from the solution. The mixture was cooled and the bis-maleate salt, mp 151°-153° was recovered by filtration.

Recrystallization from the same solvent raised the melting point to 153°-154°; $[\alpha]_D{}^{25}$ −10.8° (c, 1.0, MeOH).

Anal. Calcd. for $C_{24}H_{35}N_3O_3.2C_4H_4O_4$: C, 59.52; H, 6.71; N, 6.51. Found: C, 59.59; H, 6.55; N. 6.56.

Method C—From (S)-1-[2-(4-(2,3-epoxypropoxy)phenoxy)ethyl]-4-phenylpiperazine A solution of 7.8 g (22 mmol) (S)-1-[2-(4-(2,3-epoxypropoxy)phenoxy)ethyl]-4-phenylpiperazine in 80 ml MeOH containing 20 ml isopropylamine was heated at 75° for 2 hr. The solvent was removed in vacuo and the residue was dissolved in 100 ml MeOH containing 5.1 g (44 mmol) maleic acid. The slightly hazy solution was filtered through Celite and then was concentrated to ~60 ml, whereupon hot EtOAc was added until crystallization began. The resulting salt was recovered by filtration and washed with EtOAc to give the bis-maleate salt, mp 150°-151.5°.

Method D—From (S)-1-[2-(4-(2-hydroxy-3-N-mesylisopropylaminopropoxy)phenyl)ethyl]-4-phenylpiperazine In an inert atmosphere, 82 ml Red-al (70% solution in benzene) was added dropwise to a stirred solution of 19.2 g (39 mmol) (S)-1-[2-(4-(2-hydroxy-3-N-mesylisopropylaminopropoxy)phenoxy)-ethyl]-4-phenylpiperazine in 100 ml benzene. After heating at reflux for 3½ hr, the mixture was cooled in an ice-water bath and excess reagent was destroyed by the cautious dropwise addition of $H_2O$. The mixture was then diluted with 2 N NaOH and $CH_2Cl_2$ which resulted in the precipitation of some insoluble inorganic solids. The solids were removed by filtration through Celite and the filtrate was extracted with $CH_2Cl_2$ (3×). The organic layers were washed in turn with 2 N NaOH solution (2×) and brine (1×) and then were combined, dried ($K_2CO_3$) and evaporated to give the amine as a crystaline solid. A solution of the solids in 125 ml hot EtOAc was diluted with warm hexane (125 ml) and the product was allowed to crystallize slowly from solution. Filtration yield the amine, mp 100°-104°.

13.9 g (33.6 mmol) of the pure amine was added to a hot solution of 7.96 g (68.6 mmol) maleic acid in 100 ml MeOH. Hot EtOAc was added in portions to the refluxing solution until crystallization of the salt began. After cooling, the mixture was filtered to give the bis-maleate salt, mp 152°-154°.

EXAMPLE 32

(S)-1-[2-(4-(2-Hydroxy-3-tert-butylaminopropoxy)phenoxy) ethyl]-4-phenylpiperazine and its bis-maleate salt A solution of 7.8 g (22 mmol) of (S)-1-[2-(4-(2,3-epoxypropoxy)phenoxy)ethyl]-4-phenylpiperazine in 80 ml MeOH containing 25 ml tert-butylamine. The solvent was removed under reduced pressure to give an oily residue which crystallized on standing. The crude amine was dissolved in 60 ml hot MeOH containing 5.1 g (44 mmol) maleic acid. Almost immediately a crystalline solid began to form. The mixture was cooled and filtered to yield the bis-maleate, mp 180°-182°. A second crop, mp 172°-175° recovered from the mother liquors, was recrystallized from MeOH to give the salt, mp 179°-181°.

The first crop was recrystallized from MeOH to give the analytically pure salt, mp 182°-184°; $[\alpha]_D^{25} -6.03°$ (c, 0.58, $H_2O$).

Anal. Calcd. for $C_{25}H_{37}N_3O_3 \cdot 2C_4H_4O_4$: C, 60.01; H, 6.88; H, 6.37. Found: C, 60.05; H, 6.97; N, 6.32.

1.3 g of the second crop bis-maleate salt from above was dissolved in 60 ml warm $H_2O$ and basified with 5 ml 2 N NaOH. The resulting solid was recovered by filtration, washed with water and dissolved in $CH_2Cl_2$. The $CH_2Cl_2$ solution was dried ($K_2CO_3$) and evaporated to give the free amine as a white solid. Crystallization from EtOAc furnished the pure base as a monohydrate, mp 82°-84°.

Anal. Calcd. for $C_{25}H_{37}N_3O_3 \cdot H_2O$: C, 67.39; H, 8.82; N, 9.43; $H_2O$, 4.21. Found: C, 67.22; H, 8.65; N, 9.13; $H_2O$, 4.02.

EXAMPLE 33

(S)-1-[2-(4-(2-Hydroxy-3-isopropylaminopropoxy)phenoxy)ethyl]-4-(2-methoxyphenyl)piperazine and its bis-maleate salt 9.33 g 4 N NaOH (37.3 mmol) was added to a solution of 8.4 g (37.3 mmol) (S)-1-(4-hydroxyphenoxy)-2-hydroxy-3-isopropylaminopropane and 9.0 g (35.4 mmol) 1-(2-chloroethyl)-4-(2-methoxyphenyl)piperazine in 75 ml DMSO and the mixture was heated at 60° for 90 min. After cooling, the mixture was diluted with 200 ml 0.5 N NaOH and extracted using benzene (3×200 ml). The organic extracts were washed in turn with $H_2O$ (2×100 ml) and then were combined, dried ($K_2CO_3$) and evaporated.

8.6 g (74 mmol) of maleic acid was added to a solution of the residue in 40 ml MeOH and EtOAc was added to the cloud point. The compound did not crystallize and thus the solvents were removed in vacuo. The crude salt was redissolved in EtOH (40 ml) and EtOAc was again added just to the cloud point. The resulting crude solid was recrystallized from EtOH-EtOAc to give essentially pure product as its bis-maleate salt, mp 105°-110°. The analytically pure salt [mp 115°-117°; $[\alpha]_D^{25} -10.4°$ (c, 1.0, MeOH] was obtained from the same solvents.

Anal. Calcd. for $C_{25}H_{37}N_3O_4 \cdot 2C_4H_4O_4$: C, 58.66; H, 6.71; N, 6.22. Found: C, 58.52; H, 6.77; N, 6.50.

0.7 g of the bis-maleate salt was dissolved in 5 ml $H_2O$ and basified with 3 ml 1 N NaOH. The resulting crude free base was filtered off and dried. Crystallization from ether afforded the analytically pure material, mp 89°-90.5°.

Anal. Calcd. for $C_{25}H_{37}N_3O_4$: C, 67.69; H, 8.41; N, 9.47. Found: C, 67.97; H, 8.56; N, 9.42.

EXAMPLE 34

1-(2-Bromoethoxy)-4-(2-propenyloxy)benzene

To a solution of 45.0 g of 4-(2-bromoethoxy)-phenol (0.207 mol) in 310 ml of acetone was added 54 ml of allyl bromide (0.619 mol) and 45.0 g of anhydrous potassium carbonate (0.326 mol). The reaction mixture was stirred under reflux for eleven hours and was cooled and poured into 2500 ml of water. The mixture was extracted twice with 3:1 ether:methylene-chloride, and the organic layers were washed twice with 1 N NaOH, once with $H_2O$, dried ($Na_2SO_4$) and concentrated to dryness under reduced pressure to yield a colorless oil. The analytical sample was prepared by crystallization from hexane to give colorless crystals, mp 27°-28°.

Anal. Calcd. for $C_{11}H_{13}BrO_2$: C, 51.38; H, 5.10; Br, 31.08. Found: C, 51.63; H, 5.27; Br, 31.22.

EXAMPLE 35

(R,S)-1-(2-Bromoethoxy)-4-(2,3-epoxypropoxy)benzene

To a solution of 48.0 g of 1-(2-bromoethoxy)-4-(2-propenyloxy)benzene (0.186 mol) in 960 ml of acetone and 125 ml of water was added 2.0 ml of 70% perchloric acid. To this stirred reaction mixture was added portionwise over a 12 min period 38.4 g (0.278 mol) of N-bromoacetamide. The stirred reaction mixture was maintained at 22° for 2½ hr and was then treated with solid $NaHSO_3$ until a negative starch-KI reaction was achieved. The acetone was next removed in vacuo, and the residue was diluted with 1 l of water. The mixture was extracted twice with methylene chloride and the organic layers were washed with water, dried ($Na_2SO_4$) and concentrated to dryness under reduced pressure to yield the bromohydrin intermediate as a red oil.

The crude oil was redissolved in 1300 ml methanol and treated with 375.0 ml of 1 N NaOH. The reaction mixture was allowed to stand for two hours at room temperature under argon at which time the methanol was removed in vacuo and the residue was diluted with 1 l of water. The resulting precipitate was filtered and washed well with water. It was then redissolved in methylene chloride, dried ($Na_2SO_4$), and concentrated to dryness under reduced pressure to yield a pale yellow solid. The crude solid was chromatographed on a column of Florisil using 1:1 $C_6H_6$—$CH_2Cl_2$ as eluent. The eluted fractions were combined and concentrated to dryness to yield a yellow solid, mp 50°-61.5°. The solid was then rechromatographed through a column of Florisil in benzene and eluted again with 1:1 $C_6H_6$—$CH_2Cl_2$ to yield a colorless solid, mp 56°-62°. Crystallization from ether:hexane yielded the end product as colorless crystals, mp 59°-62°. A second crop from the mother liquors yielded product, mp 58.5°-61.5°. Crystallization from ether:hexane gave the analytical sample, mp 62°-64°.

Anal. Calcd. for $C_{11}H_{13}BrO_3$: C, 48.37; H, 4.80; Br, 29.26. Found: C, 48.40; H, 4.86; Br, 29.32.

EXAMPLE 36

(R,S)-1-(2-Bromoethoxy)-4-[2-hydroxy-3-isopropylaminopropoxy]benzene

To a stirred suspension of 15.0 g of (R,S)-1-(2-bromoethoxy)-4-(2,3-epoxypropoxy)benzene (0.055 mol) in 150 ml of methanol was added 10.2 ml of isopropylamine (0.122 mol). The reaction mixture was stirred and heated in an argon atmosphere at 55° for 3 hours and was then cooled to room temperature. The solvent was removed in vacuo to yield a pale yellow oil which crystallized on standing. The product was crystallized twice from methylene chloride-hexane to afford the end product as colorless crystals, mp 83°-87.5°.

Crystallization from methylene chloride-hexane gave the analytical sample, mp 87°-89.5°.

Anal. Calcd. for $C_{14}H_{22}BrNO_3$: C, 50.61; H, 6.67; N, 24.05; Br, 4.22. Found: C, 50.50; H, 6.71; N, 24.05; Br, 4.09.

EXAMPLE 37

(R,S)-1-(4-Benzyloxyphenoxy)-2-hydroxy-3-isopropylaminopropane.

To a solution of 200 g (1 mol) p-benzyloxyphenol in 2.5 DMSO was added 375 ml 4 N NaOH followed by 216 ml of epichlorohydrin and the resulting mixture was stirred at room temp for 3 hr. The reaction was poured into 6 l of an ice-water mixture and extracted with $CH_2Cl_2$ (3×1 l). The organic extracts were washed in turn with $H_2O$ (3×500 ml), and then were combined, dried ($Na_2SO_4$) and evaporated to dryness. The resulting crude solid was crystallized from ether to give (R,S)-1-(4-benzyloxyphenoxy)-2,3-epoxypropane in two crops. A solution of 135 g (0.527 mol) of the above epoxide in 1 l MeOH containing 135 ml isopropylamine was refluxed for 90 minutes. The solvents were then removed under reduced pressure and the residual solid was triturated with ether to give the end product amine, mp 99°-100°. A second crop, mp 98°-100°, was obtained by concentration of the ether extracts.

A small sample (1 g) of the second crop was recrystallized from ether to give the analytical sample, mp 100°-101°.

Anal. Calcd. for $C_{19}H_{25}NO_3$: C, 72.35; H, 7.99; N, 4.44. Found: C, 72.42; H, 7.99; N, 4.41.

EXAMPLE 38

(R,S)-1-(4-Hydroxyphenoxy)-2-hydroxy-3-isopropylaminepropane (R,S)-1-(4 Benzyloxyphenoxy)-2-hydroxy-3-isopropylaminopropane (124 g) in MeOH (1 l) containing 5 g 10% Pd/C was hydrogenated (21°; atmospheric pressure). The uptake of $H_2$ (total 9.6 l) essentially stopped after 1 hr. The catalyst was removed by filtration (Celite) and the filtrate was concentrated to dryness in vacuo. The resulting solid residue was crystallized from ethanol to give the end product, mp 158°-159°. A second crop of product was obtained by concentration of the mother liquor.

Anal. Calcd. for $C_{12}H_{19}NO_3$: C, 63.98; H, 8.50; N, 6.22. Found: C, 64.03; H, 8.62; N, 6.09.

EXAMPLE 39

(R,S)-1-[2-(4-(2-Hydroxy-3-(isopropylaminopropoxy)-phenoxy)ethyl]-4-phenylpiperazine and its bis-maleate salt Method A—From the product of Example 36.

A stirred mixture of 9.0 g of (R,S)-1-(2-bromoethoxy)-4-[2-hydroxy-3-isopropylaminopropoxy]benzene (0.027 mol) and 9.0 g (0.055 mol) of N-phenylpiperazine in 135 ml of ethanol was refluxed under argon for seven hours. The reaction mixture was then cooled to room temp and the solvent was removed in vacuo. The residue was dissolved in benzene and washed twice with 1 N NaOH solution and once with water. The dried ($Na_2SO_4$) organic layer was concentrated to dryness under reduced pressure to yield a crude solid which was crystallized twice from ether:hexane to yield the end product base as colorless crystals, mp 182.5°-186.5°. Crystallization from methylene chloride-ether gave the analytical sample, mp 87°-89.5°.

Anal. Calcd. for $C_{24}H_{35}N_3O_3$: C, 69.70; H, 8.53; N, 10.16. Found: C, 69.57; H, 8.45; N, 10.02.

A solution of 7.70 g (18.6 mmol) of the free base in 150 ml of absolute ethanol was treated with a solution of 5.10 g (43.9 mmol) of maleic acid in 80 ml of absolute ethanol. The reaction mixture was heated on the steam bath for two minutes and was then allowed to cool slowly to room temp. The solvent was removed in vacuo to yield a pale yellow solid which was crystallized twice from methanol-ethyl acetate to yield the bis-maleate salt as pale yellow crystals, mp 141.5°-144°.

Crystallization from methanolethyl acetate gave the analytical sample as colorless crystals, mp 142°–144°.

Anal. Calcd. for $C_{32}H_{43}N_3O_{11}$: C, 59.52; H, 6.71; N, 6.51. Found: C, 59.56; H, 6.94; N, 6.53.

EXAMPLE 40

The end product of Example 39

Method B—From the end product of Example 38

To a stirred mixture of (R,S)-1-(4-hydroxyphenoxy)-2-hydroxy-3-isopropylaminopropane (4.5 g; 20 mmol) and 1-(2-chloroethyl)-4-phenylpiperazine (4.6 g; 20.5 mmol) in 35 ml DMSO was added 5.0 ml 4 N NaOH (20 mmol). After stirring 3 hrs at 60°, the reaction mixture was cooled and partitioned between $CH_2Cl_2$ and dilute NaOH solution. The layers were separated and the aqueous layer was re-extracted with $CH_2Cl_2$ (2×). The organic layers were then washed in turn with $H_2O$ (2×) and were combined, dried ($K_2CO_3$) and evaporated in vacuo.

The crude free base thus obtained was dissolved in 75 ml MeOH containing 4.6 g (40 mmol) maleic acid and EtOAc was added portionwise to the boiling solution to the cloud point. After the solution was chilled, the resulting solid was recovered by filtration to give the bis-maleate salt. Recrystallization from MeOH-EtOAc furnished the pure salt, mp 143.5°–144°.

EXAMPLE 41

(S)-1-[6-(4-(2-Hydroxy-3-isopropylaminopropoxy)-phenoxy)hexyl]-4-piperazine

A solution of 25 g (0.128 mol) of 6-bromohexanoic acid and 12.7 g (0.125 mol) of triethylamine in 150 ml of ether was cooled (0°) and treated dropwise with 28.5 g (0.263 mol) of ethyl chloroformate. The reaction mixture was stirred for 1 hr and then filtered. To the cooled (0°) filtrate was added a solution of 21 g (0.129 mol) of N-phenylpiperazine in 50 ml of ether. The reaction mixture was then allowed to warm to room temperature for 30 min and was then washed once with 1 N NaOH solution and once with water. The dried ($Na_2SO_4$) organic layers were concentrated in vacuo to give a yellow oil which was dissolved in benzene and chromatographed on silica gel (500 g). The column was eluted with benzeneethyl acetate mixtures, the product appearing in the benzeneethyl acetate (8.5:1.5) mixtures. Evaporation of those combined mixtures gave 1-(6-bromohexanoyl)-4-phenylpiperazine.

This material (4.55 g, 13.2 mmol) was added to a solution of 4.0 g (13.2 mmol) of (S)-1-(4-hydroxyphenoxy)-2-hydroxy-3-N-mesylisopropylaminopropane in 30 ml of dimethylsulfoxide. To this stirred solution was added 3.33 ml of 4 N NaOH solution and the reaction mixture was heated at 70° for 30 min. It was then cooled, diluted with water and extracted three times with ethyl acetate. The organic layers were washed once in 1 N NaOH solution, twice with water, dried ($Na_2SO_4$) and evaporated to give the intermediate condensation product as an oil.

To this material (7.4 g, 13.2 mmol) in 62 ml of dry benzene was added dropwise 42 ml of 70% sodium bis(2-methoxyethoxy)-aluminum hydride in benzene (Red-al). The reaction mixture was refluxed for 80 min and was then cooled and treated with 40 ml of 2 N NaOH solution followed by 100 ml of $H_2O$. The mixture was extracted three times with benzene and the organic layers were washed twice with water, dried ($Na_2SO_4$) and evaporated. The residue was crystallized from methylene chloride-ether to yield the end product (free base), mp 75°–76°. Crystallization from acetonehexane gave the analytical sample, mp 78°–79°; $[\alpha]_D^{25} -3.52°$ (c, 1.0, $CHCl_3$).

Anal. Calcd. for $C_{28}H_{43}N_3O_3$: C, 71.61; H, 9.23; N, 8.95. Found: C, 71.69; H, 9.22; N, 8.79.

EXAMPLE 42

(S)-1-[6-[4-(2-Hydroxy-3-isopropylaminopropoxy)-phenoxy]hexyl]-4-phenylpiperazine dihydrochloride A solution of 4.265 g (9 mmol) of free base of Example 41 in 60 ml of ethanol was treated with 3.5 ml of 5.13 N ethanolic hydrogen chloride. The resulting solid was collected by filtration and washed with ethanol to give the end product, mp 183°–185°. Crystallization from ethanol gave the analytical sample, mp 183°–184°; $[\alpha]_D^{25} -11.4°$ (c, 0.5, $CH_3OH$).

Anal. Calcd. for $C_{28}H_{43}N_3O_3 \cdot 2$ HCl: C, 61.98; H, 8.36; Cl, 13.07; N, 7.74. Found: C, 61.69; H, 8.30; Cl, 12.85; N, 7.61.

EXAMPLE 43

(S)-1-[11-(4-(2-Hydroxy-3-isopropylaminopropoxy)-phenoxy)undecanyl]-4-phenylpiperazine To a stirred solution of 13.26 g of 11-bromoundecanoic acid (50 mmol) in 75 ml of ether was added 6.95 ml (50 mmol) of triethylamine. The stirred solution was cooled to 0° and 4.80 ml of ethyl chloroformate (50 mmol) was added dropwise. The mixture was stirred for one hour at 0° and the resulting precipitate was filtered and washed with ether.

The filtrate was recooled to 0° and a solution of 8.10 g (50 mmol) of N-phenylpiperazine in 25.0 ml of ether was added with stirring. A precipitate formed and the ice bath was removed. Stirring was continued for an additional 25 minutes at room temp and the material was then collected by filtration and was washed well with ether to yield colorless crystals, mp 70°–74°. Crystallization from methylene chloride:ether gave 1-(11-bromoundecanoyl)-4-phenylpiperazine as colorless crystals, mp 73°–75.5°. Crystallization from methylene chloride-ether gave the analytical sample, mp 73.5°–75.5°.

Anal. Calcd. for $C_{21}H_{33}BrN_2O$: C, 61.61; H, 8.13; N, 6.84; Br, 19.52. Found: C, 61.77; H, 8.14; N, 6.72; Br, 19.47.

To a stirred solution of 3.03 g (10 mmol) of (S)-1-(4-hydroxyphenoxy)-2-hydroxy-3-N-mesylisopropylaminopropane and 4.09 g of 1-(11-bromoundecanoyl)-4-phenylpiperazine (10 mmol) in 20 ml of dimethylsulfoxide was added 3.0 ml (12 mmol) of 4 N NaOH solution. The reaction mixture was stirred and heated at 75°–78°, under argon for 35 minutes and was then cooled to room temperature and diluted with 100 ml of cold water. The mixture was extracted twice with ethyl acetate and the organic layers were washed once with 1 N NaOH, twice with water, and dried ($Na_2SO_4$). The solvent was evaporated to dryness under reduced pressure to yield a colorless oil.

To a stirred solution of 6.50 g of this oil (10.4 mmol) in 55.0 ml benzene was added 36.6 ml of 70% sodium bis(2-methoxyethoxy)-aluminum hydride in benzene (Red-al). The reaction mixture stirred under reflux (argon atmosphere) for 2¼ hr, then cooled to room temp and treated with 35 ml of 2 N NaOH and 100 ml of water. The mixture was extracted twice with benzene and the organic layers were washed twice with water, dried (K₂CO₃), and concentrated to dryness under reduced pressure to yield a colorless solid. The material was crystallized from acetone to yield the end product (free base) as colorless crystals, mp 99°–103°. Crystallization from acetone gave the analytical sample, mp 101.5°–104°; $[\alpha]_D^{25} -2.82°$ (c, 1.13, CHCl₃).

Anal. Calcd. for $C_{33}H_{53}N_3O_3$: C, 73.42, H, 9.90; N, 7.79. Found: C, 73.62; H, 9.91; N, 7.62.

EXAMPLE 44

(S)-1-[11-[4-(2-Hydroxy-3-isopropylaminopropoxy)-phenoxy]undecanyl]-4-phenylpiperazine dihydrochloride To a warm (40°) solution of 2.83 g (5.2 mmol) of the free base of Example 43 in 95 ml of absolute ethanol was added at a rapid dropwise rate with swirling 2.03 ml (10.4 mmol) of 5.13 N ethanolic hydrogen chloride solution. The mixture was then cooled to 0° and the resulting colorless crystals were collected by filtration to yield the end product, mp 193°–196°. Crystallization from ethanol gave the analytical sample, mp 193.5°–196°; $[\alpha]_D^{25} -7.52°$ (c, 0.5, CH₃OH).

Anal. Calcd. for $C_{33}H_{53}N_3O_3.2$ HCl: C, 64.69; H, 9.05; N, 6.86; Cl, 11.57. Found: C, 64.60; H, 9.10; N, 6.88; Cl, 11.37.

EXAMPLE 45

(S)-1-(2-Hydroxyphenoxy)-2-hydroxy-3-N-mesylisopropylaminopropane 39.9 g (0.362 mol) of catechol was added to a solution of 14.5 NaOH (362 mmol) in 45 ml H₂O and the mixture was stirred under argon. The pasty mixture was diluted with 100 ml of DMSO and after 10 min, a solution of 52.3 g (0.181 mol) of (S)-1-mesyloxy-2-hydroxy-3-N-mesylisopropylaminopropane in 100 ml of DMSO was added. The solution was stirred at 80° under argon for 2½ hr and then it was cooled and diluted with 400 ml 1 N NaOH. The solution was extracted with CH₂Cl₂ (3×250 ml) and the organic extracts were backwashed (1×) with dilute NaOH solution. The combined basic aqueous extracts were acidified using 70 ml concentrated HCl and extracted with CH₂Cl₂ (2×500 ml). The organic extracts were then washed in turn with water (5×500 ml) and then were combined, dried (Na₂SO₄) and evaporated to give the essentially pure monoalkylated end product as an oil.

EXAMPLE 46

(S)-1-[2-(3-Bromopropoxy)phenoxy]-2-hydroxy-3-N-mesylisopropylaminopropane

A mixture of 15 g (49.5 mmol) (S)-1-(2-hydroxyphenoxy)-2-hydroxy-3-N-mesylisopropylaminopropane, 30.6 g (~150 mmol) 1,3-dibromopropane, and 10.6 g K₂CO₃ in 60 ml acetone was stirred under reflux overnight. The reaction was diluted with water and extracted with CH₂Cl₂ (4×). The CH₂Cl₂ extracts were washed in turn with 1 N NaOH solution and then were combined, dried (Na₂SO₄), and concentrated to dryness in vacuo to give 18.5 g of an oil. The oil was chromatographed on 200 g silica gel made up in hexane. The column was eluted successively with hexane, benzene, benzene-Et₂O (19:1), benzene-Et₂O (9:1) and benzene-Et₂O (3:1). The fractions eluted with benzene-Et₂O (9:1) and (3:1) were combined and evaporated to dryness to give chromatographically pure product, mp 95°–96°. Crystallization from EtOAc-hexane furnished the pure compound, mp 98°–99°.

The analytical sample, mp 98°–100°; $[\alpha]_D^{25} -4.99°$ (c, 1.0, CHCl₃) was obtained from smaller experiment using the same solvent system.

Anal. Calcd. for $C_{16}H_{26}BrNO_5S$: C, 45.29; H, 6.18; N, 3.30; S, 7.56; Br, 18.83. Found: C, 14.80; H, 6.16; N, 3.30; S, 7.60; Br, 18.32.

EXAMPLE 47

(S)-1-[3-(2-(2-Hydroxy-3-N-mesylisopropylaminopropoxy)phenoxy)propyl]-4-phenylpiperazine A mixture of 10.5 g (24.7 mmol) (S)-1-[2-(3-bromopropoxy) phenoxy]-2-hydroxy-3-N-mesylisopropylaminopropane and N-phenylpiperazine (4.42 g; 27.3 mmol) in 50 ml ethanol was left at room temperature for ~3 days. Tlc showed the reaction to be ~50% completed but the ratio of starting materials and product did not change after 4 hrs at reflux. 4.0 ml 4 N NaOH was added and the reaction heated for 2 hours, and than an additional 1.5 ml 4 N NaOH [total used=22 equiv (95% of theory)] was added. After another 60 min at reflux, the reaction was cooled and evaporated. The residue was diluted with water and extracted with EtOAc. The EtOAc extract was dried (K₂CO₃) and evaporated to give an oil. The oil was chromatographed over 200 g silica gel. The column was eluted with benzene and benzene-EtOAc mixtures (19:1; 9:1; 3:1 and 1:1) and then the product was eluted from the column using ethyl acetate to give the end product. Crystallization from ether afforded product in two crops, (mp 84°–85° and 82°–84°).

Recrystallization of a small amount from ether (2×) furnished the analytically pure material, mp 85°–86°; $[\alpha]_D^{25} -1.0°$ (c, 1.0, CHCl₃).

Anal. Calcd. for $C_{26}H_{39}N_3O_5S$: C, 61.76; H, 7.77; N, 8.31; S, 6.34. Found: C, 61.92; H, 7.85; N, 8.26; S, 6.29.

EXAMPLE 48

(S)-1-[3-(2-(2-Hydroxy-3-N-mesylisopropylaminopropoxy)phenoxy)propyl]-4-phenylpiperazine and its dihydrochloride 22 ml Red-al (60% solution in benzene) was added dropwise at first and then, once the bubbling had ceased, more rapidly to a stirred solution of 6.2 g (12.25 mmol) (S)-1-[3-(2-(2-hydroxy-3-N-mesylisopropylaminopropoxy)phenoxy)propyl]-4-phenylpiperazine in 100 ml dry benzene. The reaction was refluxed for 5 hrs under argon and then it was left overnight at room temp. Excess reagent was decomposed by the dropwise addition of 25 ml 2 N NaOH and then it was diluted with water (25 ml). The benzene layer was separated and the aqueous layer was extracted with benzene (2×). The benzene layers were washed in turn with 2 N NaOH solution (1×) and brine (2×). The combined extracts were dried (K₂CO₃) and evaporated under reduced pressure to give the crude amine. Crystallization from acetone-hexane gave solids in two crops, which when recrystallized from the same solvent system afforded the pure amine, mp 87°–88°.

Anal. Calcd. for $C_{25}H_{37}N_3O_3$: C, 70.23; H, 8.72; N, 9.83. Found: C, 70.27; H, 8.74; N, 9.70.

3.5 g of the amine in 150 ml absolute EtOH was treated with 2.2 molar equivalents of ethereal HCl and then the solution was diluted to 400 ml with ether. The resulting crystalline solid was collected by filtration to give the dihydrochloride salt, mp 192°–193°.

The analytically pure material, mp 192°–193°; $[\alpha]_D^{25} -5.39°$ (c, 1.0, H₂O) was obtained by recrystallization from EtOH.

Anal. Calcd. for $C_{25}H_{37}N_3O_3 \cdot 2HCl$: C, 59.99; H, 7.85; N, 8.40; Cl, 14.17. Found: C, 60.20; H, 8.13; N, 8.25; Cl, 14.28.

EXAMPLE 49

(S)-1-[6-(2-(2-Hydroxy-3-N-mesylisopropylamino)-propoxy)phenoxy)hexanoyl]-4-phenylpiperazine 8.0 ml 4 N NaOH (32 mmol) was added to a solution of 9.5 g (31.35 mmol) (S)-1-(2-hydroxyphenoxy)-2-hydroxy-3-N-mesylisopropylaminopropane and 10.9 (32 mmol) 1-(6-bromohexanoyl)-4-phenylpiperazine in 70 ml DMSO and the mixture was heated at 80° under argon for 50 min. The reaction was cooled and poured into 500 ml H₂O and extracted with benzene (2×250 ml). The benzene extracts were washed in turn with 1 N NaOH (2×) and H₂O (1×), and then were combined, dried (K₂CO₃) and evaporated to give an oil. The oil was chromatographed on 200 g silica gel made up in benzene. The fractions eluted with EtOAc:benzene (1:1 and 3:2) were combined and evaporated to yield essentially pure product as an oil.

A small sample was purified for analysis by preparative tlc.

Anal. Calcd. for $C_{29}H_{43}N_3O_6S$: C, 62.01; H, 7.71; N, 7.48; S, 5.71. Found: C, 62.02; H, 7.98; N, 7.23; S, 5.46.

EXAMPLE 50

(S)-1-[6-(2-(2-Hydroxy-3-isopropylaminopropoxy)-phenoxy)hexyl]-4-phenylpiperazine and its fumarate salt In an inert atmosphere 70 ml Red-al (70% solution in benzene) was added cautiously at first and then more rapidly to a stirred solution of 11.4 g (20.28 mmol) (S)-1-[6-(2-(2-hydroxy-3-N-mesylisopropylaminopropoxy)-phenoxy)hexanoyl]-4-phenylpiperazine in 100 ml dry benzene. The reaction was then heated and stirred under reflux for 90 minutes. 50 ml 2 N NaOH solution was then added carefully to the cooled reaction mixture, followed by 100 ml H₂O and 300 ml benzene. The aqueous layer was separated and extracted with benzene (2×300 ml). The benzene layers were then backwashed in turn with water (2×100 ml). The pooled organic extracts were dried (K₂CO₃) and concentrated to give an oil which solidified when it was evaporated in vacuo from acetone. The residue was crystallized from acetone-hexane to give the pure amine, mp 69°–71°. Recrystallization from acetone-hexane gave the analytical sample, mp 69°–71°; $[\alpha]_D^{25} +3.5°$ (c, 1.0, CHCl₃).

Anal. Calcd. for $C_{28}H_{43}N_3O_3$: C, 71.61; H, 9.23; N, 8.95. Found: C, 71.82; H, 9.38; N, 8.80.

4.0 g (8.55 mmol) of the amine and 0.99 g (8.55 mmol) of fumaric acid were dissolved in 25 ml MeOH at room temp and then the solution was diluted with 50 ml EtOAc. The resulting fumarate salt which slowly crystallized from solution was collected by filtration and was washed with EtOAc to yield the salt, mp 163°–165°.

The analytically pure specimen of fumarate, mp 164°–165° was obtained by recrystallization from MeOH-EtOAc.

Anal. Calcd. for $C_{28}H_{43}N_3O_3 \cdot C_4H_4O_4$: C, 65.62; H, 8.09; N, 7.17. Found: C, 65.36; H, 7.92; N, 7.12.

EXAMPLE 51

Bromohydrins from 4-allyloxyphenylacetic acid

A solution of 5.00 g (0.0260 mol) of 4-allyloxyphenylacetic acid in 25 ml of acetone and 8 ml of water was cooled in an ice bath and treated with 5.00 g (0.0362 mol) of N-bromosuccinimide (NBS). The resulting mixture was allowed to warm to room temperature slowly and after 2.5 hour, an additional 0.5 g. of NBS was added. After a total of 3.5 hours, the reaction mixture was diluted with 150 ml of water and a small amount of citric acid. The product was extracted with methylene chloride and after evaporation of the solvent, gave a crude solid. Recrystallization from ethyl acetate-hexane gave a mixture of bromohydrins containing the end-products, m.p. 85°–99°. Several crystallizations from ethyl acetate-hexane gave an analytically pure sample of one of the isomers, m.p. 128°–133°.

EXAMPLE 52

(R,S)-4-(2,3-Epoxypropoxy)phenylacetic acid

Method A

A solution of 1.66 g (5.74 mmol) of the mixture of bromohydrins obtained in Example 51 in 100 ml of methanol and 5 ml of 4 N sodium hydroxide solution was stirred at room temperature for 2 hours. The resulting mixture was diluted with 1 M citric acid to pH 3 and extracted with methylene chloride. Crystallization of the crude product from methanol-water gave the end-product. Recrystallization from methanol-ether gave the analytical sample, m.p. 73°–77°.

Anal. ($C_{11}H_{12}O_4$) C, H.

Method B

A solution of 2.00 g (10.4 mmol) of 4-allyloxyphenylacetic acid and 1.6 g. of NBS in 10 ml. of acetone and 4 ml. of water was stirred 30 minutes at 0° and allowed to warm to room temperature. After an hour 0.2 g of NBS were added and after a total of 2.5 hour, the mixture was cooled in an ice bath and 5.5 ml of 4 N sodium hydroxide were added. The mixture was warmed to room temperature, stirred one hour, and diluted with water, ice, and 10% citric acid solution. The solution was extracted with methylene chloride and the methylene chloride layers afforded the product as an off-white solid, m.p. 72°–76°.

EXAMPLE 53

Methyl 4-allyloxyphenyl acetate

A mechanically stirred suspension of 101.54 g (0.528 mol) of 4-allyloxyphenylacetic acid, 70 ml (1.12 mol) of iodomethane, and 100 g (0.756 mol) of potassium carbonate in 210 ml. of hexamethylphosphoramide was left at room temperature overnight. The resulting mixture was diluted with 1 liter of ether and the ethereal solution was washed 3×300 ml water and 1×300 ml. saturated brine. The ethereal solution was concentrated and the product was distilled to give a colorless oil, b.p. 120°–135°/0.05 mm.

EXAMPLE 54

(R,S)-Methyl-4-(2,3-epoxypropoxy)phenyl acetate

Method A

To an ice cold solution of 4.50 g (0.0216 mol) of the product of Example 52 in 20 ml of dry methanol as added an excess of ethereal diazomethane. Evaporation of the resulting solution to dryness gave the ester.

Method B

A solution of 25.25 g (0.122 mol) of the product of Example 53 and 62 g (0.359 mol) of m-chloroperbenzoic acid in 200 ml of methylene chloride was stirred at room temperature. After 24 hours the reaction mixture was poured into 200 ml. of water made basic with 45% NaOH. The aqueous layer was extracted 2×300 ml $CH_2Cl_2$ and the combined organic layers were washed 2×200 ml. $H_2O$ and 1×200 ml. brine. The crude product was evaporatively distilled to give the end-product, b.p. 180°–185°/0.1 mm. A portion was purified by preparative layer chromatography and distilled.

Anal. ($C_{12}H_{14}O_4$) C, H.

EXAMPLE 55

Methyl 4-(2-hydroxy-3-isopropylaminopropoxy)phenyl acetate

A solution of 55.29 g (0.249 mol) of the product of Example 54 and 27.0 ml (0.334 mol) of isopropylamine in 200 ml. of methanol was stirred overnight at room temperature. The mixture was concentrated and the residue was dissolved in excess 1 M citric acid. The aqueous solution was washed 3×100 ml. $CH_2Cl_2$ and was made basic by addition of 45% NaOH followed by extraction with 4×100 ml $CH_2Cl_2$. The combined extracts were washed with saturated brine and were dried ($K_2CO_3$). Evaporation gave the end-product, m.p. 72°–74°. Recrystallization from ether-hexane gave the analytical sample, m.p. 72°–74°.

Anal. ($C_{15}H_{23}NO_4$) C, H, N.

EXAMPLE 56

6-(4-Phenyl-1-piperazinyl)hexamide

A suspension of 9.85 g (0.060 mol) of phenylpiperazine, 11.6 g (0.060 mol) of 6-bromohexamide, and 6.35 g (0.060 mol) of sodium carbonate in 90 ml of toluene was heated reflux overnight. On cooling, the mixture was filtered and the filtrate was washed with water. Evaporation and crystallization of the crude product from methylene chloride-hexane gave analytically pure product, m.p. 129°–130°.

Anal. ($C_{16}H_{25}N_3O$), C, H, N.

EXAMPLE 57

11-(4-Phenyl-1-piperazinyl)undecamide

A suspension of 13.1 g (0.0795 mol) of phenylpiperazine, 20.86 g (0.0795 mol) of 11-bromoundecamide and 8.45 g (0.0795 mol) of sodium carbonate in 120 ml of toluene was heated to reflux overnight. On cooling the solid which separated was collected and triturated with water to give the end-product, m.p. 128°–129°. Two recrystallizations from ethanol-ethyl acetate-hexane gave the analytical sample, m.p. 129°–130°.

Anal. ($C_{12}H_{37}N_3O$) C, H, N.

EXAMPLE 58

1-(6-Aminohexyl)-4-phenylpiperazine

A solution of 38.3 g (0.139 mol) of the product of Example 56 in 400 ml of THF was treated with 500 ml. of 1 M borane in THF. The solution was refluxed for 8 hours and was cooled in an ice bath as 42 ml. of 12 N hydrochloric acid was added carefully. The excess THF was evaporated, the aqueous solution was made basic with potassium carbonate and was extracted with $CH_2Cl_2$. Evaporation of the organic layers gave an oil which gave a single spot on silica gel TLC and was used in the next example without further purification. A portion was further characterized as its dihydrochloride salt which crystallized from ethanol, m.p. 251°–253°.

Anal. ($C_{16}H_{27}N_3.2HCl$) C, H, N.

EXAMPLE 59

1-(11-Aminoundecyl)-4-phenylpiperazine 1-(11-aminoundecyl)-4-phenylpiperazine was prepared similarly starting with 11.2 g (0.0322 mol) of the product of Example 57 to give the end-product as an oil. The dihydrochloride salt crystallized from ethanol, m.p. 197°–202°.

Anal. ($C_{21}H_{37}N_3.2HCl$) C, H; N, calcd. 10.39; fd 9.87.

EXAMPLE 60

4-[(2-Hydroxy-3-isopropylaminopropoxy)phenyl]-N-[2-(4-phenyl-1-piperazinyl)ethyl]acetamide dihydrochloride An intimate mixture of 5.00 g (0.0178 mol) of the product of Example 55 and 4.00 g (0.0190 mol) of 1-(2-aminoethyl)-4-phenylpiperazine* was heated to a bath temperature of 140°–145° overnight. The resulting solid was triturated with etherbenzene to give a tan solid, m.p. 100°–106°. Conversion to the hydrochloride salt gave the dihydrochloride salt, m.p. 173°–177°. Two recrystallizations from ethanol-ethyl acetate gave the analytical sample, m.p. 178°–181°.

Anal. ($C_{26}H_{38}N_4O_3.2HCl$) C, H, N, Cl.

*S. Hayao and R. N. Schect, *J. Org. Chem.*, 26, 3414 (1961).

EXAMPLE 61

4-[(2-Hydroxy-3-isopropylaminopropoxy)phenyl]-N-[6-(4-phenyl-1-piperazinyl)hexyl]acetamide dihydrochloride An intimate mixture of 10.0 g (0.0384 mol) of the product of Example 58 and 10.0 g (0.0355 mol) of the product of Example 55 was heated to a bath temperature of 140° overnight. The crude brown solid was dissolved in $CH_2Cl_2$ and ether was added to precipitate a waxy solid. This material was passed through 50 g of grade III basic alumina eluting with 1% methanolethyl acetate to give a colorless wax which displayed a single spot on TLC. For conversion to the hydrochloride salt, a total of 9.1 g of material obtained as above was divided into portions of 6 g and 3.1 g and the 6 g portion was treated with excess hydrochloric acid and evaporated to dryness under high vacuum. This oil was taken up in alcohol and the 3.1 g portion was added. The resulting solution was concentrated and the residue was crystallized from ethanol-ether to give the end-product, m.p. 124°–6° (decomp). The analytical sample was obtained from ethanol-ether, m.p. 123°–126° (decomp).

Anal. ($C_{30}H_{46}N_4O_3.2HCl$) C, H, N, Cl.

EXAMPLE 62

4-[[2-Hydroxy-3-(isopropylaminopropoxy)phenyl]-N-[11-(4-phenyl-1-piperazinyl)undecyl]acetamide and its dihydrochloride An intimate mixture of 9.4 g (0.030 mol) of the product of Example 59 and 8.45 g (0.030 mol) of the product of Example 55 were heated overnight at a bath temperature of 140°. The resulting brown solid was crystallized from methylene chloride-ether to give the free base, m.p. 107°–109°. A second crop, m.p. 101°–105° was obtained from the filtrate. The two crops were combined and acidified with hydrochloric acid to give a solid which was recrystallized from isopropanol to give the salt, m.p. 146°-150°.

Anal. ($C_{35}H_{56}N_4O_3.2HCl$) C, H, N, Cl.

EXAMPLE 63

(S)-4-(Dihydroxypropoxy)phenylacetic acid, methyl ester

Sodium (2.3 g; 0.1 mol) was dissolved in 500 ml anhydrous MeOH and to this was added a solution of 194.3 g (1.17 mol) 4-hydroxyphenylacetic acid, methyl ester in 250 ml MeOH followed by a solution of 167.3 g. (1.018 mol) (S)-1,2-epoxy-3-benzyloxypropane in 250 l MeOH. The solution was stirred under reflux for 12 hours. The cooled solution was treated with 8.3 ml (0.1 mol) of concentrated HCl and the methanol was removed in vacuo. The crude product was dissolved in benzene and washed with 2×200 ml portions of cold 1 N NaOH solution and with $H_2O$ (1×300 ml). The aqueous layers were backwashed with benzene (2×500 ml). The combined organic layers were dried ($Na_2SO_4$) and evaporated in vacuo to give crude (S)-4-(3-benzyloxy-2-hydroxypropoxy)phenyl acetic acid, methyl ester.

The crude ester was then dissolved in 1 liter acetic acid containing 20 ml concentrated HCl and the mixture was hydrogenated over 10 g 10% Pd/C at normal temperature and pressure. After ~100 minutes the absorption of $H_2$ ceased abruptly (total uptake ~23.3 liters). The catalyst was removed by filtration through Celite and the filtrate was evaporated to dryness under reduced pressure. Since the product had undergone partial acetylation during the hydrogenolysis, it was dissolved in 1 liter 1 N methanolic HCl and left at room temperature for 1 hour. Evaporation of the solvent furnished the diol product as a white solid.

Crystallization of a small sample from ether-hexane furnished the analytically pure material, m.p. 64°-66°; $[\alpha]_D^{25}+6.55°$ (c, 1.0, EtOH).

Anal. Calcd. for $C_{12}H_{16}O_5$: C, 59.99; H, 6.71. Found: C, 60.14; H, 6.75.

EXAMPLE 64

(R)-4-(2-Acetoxy-3-chloropropoxy)phenylacetic acid methyl ester

A stirred mixture of 223.3 g (0.916 mol) (S)-4-(2-dihydroxypropoxy)phenylacetic acid, methyl ester, 3.0 g benzoic acid (0.024 mol) and 165 g (1.375 mol) trimethylorthoacetate was heated in an oil bath at 80°. Methanol was distilled from the reaction as it was formed. After 30 minutes, the reaction was cooled and the product was partitioned between 1 liter $CH_2Cl_2$ and 300 ml cold saturated $NaHCO_3$ solution. The organic extract was washed with an additional 200 ml. $NaHCO_3$ solution and then aqueous layers were backwashed with $CH_2Cl_2$ (1×200 ml). The combined $CH_2Cl_2$ extracts were dried and evaporated to give the cyclic orthoacetate.

Without further purification this material (0.895 mol) was dissolved in 750 ml dry $CH_2Cl_2$ followed by the addition of 151 ml (1.16 mol) of trimethylchlorosilane. The resulting solution was heated at reflux for ~45 minutes, whereupon the solvent and excess reagent was removed in vacuo to give the chloroacetate as an oil.

A small portion of the product (1 g) was purified for analysis by chromatography on silica gel to give 950 mg of pure material, $[\alpha]_D^{25}-23.86°$ (c, 1.0, MeOH).

Anal. Calcd. for $C_{14}H_{17}ClO_5$: C, 55.91; H, 5.70; Cl, 11.79. Found: C, 55.90; H, 6.04; Cl, 11.50.

EXAMPLE 65

(R)-4-(2,3-Epoxypropoxy)phenylacetic acid

A cold solution of 63 g (1.575 mol) NaOH in 200 ml $H_2O$ was added with stirring over ~15 minutes to a previously chilled solution (0°) of 135 g (0.45 mol) crude (R)-4-(2-acetoxy-3-chloropropoxy)phenylacetic acid, methyl ester in 500 ml MeOH. The reaction temperature did not exceed 10° during the addition, and was then maintained at 0°-5° for 50 minutes and 10°-15° for an additional 20 minutes. The reaction was then rechilled and acidified using a solution of 32 ml concentrated $H_2SO_4$ (1.15 equiv) in 200 ml. $H_2O$. Some MeOH (~250 ml) was removed by concentration of the reaction mixture in vacuo (bath temperature ~25°) and then the solution was extracted with benzene (4×1 liter). The benzene layers were washed in turn with brine (1×250 ml) and were combined, dried ($Na_2SO_4$) and concentrated to 500 ml in vacuo. The benzene solution was warmed to ~40° and diluted to the cloud point with warm hexane and then it was stored at 0° for several hours. The resulting crystalline material was collected by filtration to give the epoxy acid end product, m.p. 70°-72°; $[\alpha]_D^{25}+10.6°$ (c, 1.0, MeOH). Concentration of the mother liquors gave additional epoxy acid.

Anal. Calcd. for $C_{11}H_{12}O_4$: C, 63.45; H, 5.81. Found: 63.27; H, 5.89.

EXAMPLE 66

(R)-4-(2,3-Epoxypropoxy)phenylacetic acid, cyanomethyl ester 20.8 g (0.1 mol) of (R)-4-(2,3-epoxypropoxy)phenylacetic acid was suspended in 30 ml chloroacetonitrile and cooled to ~10° in an ice water bath. Triethylamine (16 ml) was added to the stirred mixture at a rapid dropwise rate. The cooling bath was removed and after 30 minutes the temperature had risen to 30°. The temperature was maintained at 25°-30° by the intermittent use of the cooling bath. After 90 minutes the reaction was partitioned between toluene and $H_2O$. The organic phase was washed with saturated $NaHCO_3$ solution and with water and then the aqueous layers were backwashed with toluene. The toluene extracts were combined, dried ($MgSO_4$) and evaporated to give the cyanomethyl ester end product as an oil. This material was used without further purification.

EXAMPLE 67

(R)-4-(2,3-Epoxypropoxy)phenyl-N-[2-(4-phenyl-1-piperazinyl)ethyl]acetamide

A mixture of 10.7 g (52.1 mmol) 1-(2-aminoethyl)-4-phenylpiperazine and 13.5 g (54.6 mmol) (R)-4-(2,3-epoxypropoxy)phenylacetic acid, cyanomethyl ester in 125 dry THF was stirred at room temperature for 40 hours. The solvent was removed in vacuo and the residue was triturated with ether to give the crude amide as a white solid. The solid was dissolved in 35 ml. $CH_2Cl_2$ and placed on a column of 170 g Woelm basic alumina (grade 3) made up in $CHCl_2$. Elution with 1 liter $CH_2Cl_2$ furnished essentially pure material. Crystallization from acetone afforded the end product, m.p. 124°-125°. A second crop, m.p. 121°-123° was obtained from the mother liquors.

The analytical sample had been obtained from a previous batch by recrystallization from MeOH-H$_2$O to give pure material, m.p. 123°-124°; [α]$_D^{25}$+5.64° (c, 1.0, MeOH).

Anal. Calcd. for C$_{23}$H$_{29}$N$_3$O$_3$: C, 69.85; H, 7.39; N, 10.62. Found: C, 69.62; H, 7.40; N, 10.51.

EXAMPLE 68

(R)-4-(2,3-Epoxypropoxy)phenyl-N-[6-(4-phenyl-1-piperazinyl)hexyl]acetamide

A mixture of 9.4 g (38 mmol) (R)-4-(2,3-epoxypropoxy)phenylacetic acid, cyanomethyl ester and 9.4 g (36 mmol) 1-(6-aminohexyl)-4-phenylpiperazine in 75 ml THF was stirred for 60 hours at room temperature. The solvent was removed in vacuo and the residue was triturated with warm ether to give the crude amide. 12.4 g. of the crude amide in 25 ml CH$_2$Cl$_2$ was placed on a column of 125 g Woelm basic alumina (grade 3). Elution with 750 ml. CH$_2$Cl$_2$ furnished homogenous (tlc) material which was crystallized from acetone to give pure amide, m.p. 108°-110°.

The analytical sample, m.p. 108°-110°, was prepared in a previous run by crystallization from MeOH-H$_2$O.

Anal. Calcd. for C$_{27}$H$_{37}$N$_3$O$_3$: C, 71.81; H, 8.26; N, 9.30. Found: C, 72.03; H, 8.13; N, 9.14.

EXAMPLE 69

(S)-4-(2-Hydroxy-3-isopropylaminopropoxy)phenyl-N-[2-(4-phenyl-1-piperazinyl)ethyl]acetamide and its dihydrochloride salt A solution of 10.86 g (27.5 mmol) (R)-4-(2,3-epoxypropoxy)phenyl-N-[2-(4-phenyl-1-piperazinyl)ethyl]acetamide in 200 ml methanol containing 100 ml isopropylamine was refluxed for 90 minutes. The solution was evaporated to dryness and triturated with hot ether to give the amine, m.p. 121°-123°.

Crystallization of a small portion from EtOH-EtOAc furnished the analytically pure material, m.p. 123°-124°; [α]$_D^{25}$-0.8° (c, 1.0, MeOH).

Anal. Calcd. for C$_{26}$H$_{38}$N$_4$O$_3$: C, 68.69; H, 8.43; N, 12.32. Found: C, 68.90; H, 8.66; N, 12.15.

A portion of the above amine (8 g) was dissolved in 50 ml EtOH and treated with 35 ml 1.73 N methanolic HCl (60 mmol) and evaporated to dryness. Residue was swirled down 2x from ethanol solution which removed the excess HCl. The residue was then redissolved in 50 ml EtOH and the remaining portion of the above amine (4 g) was added. Upon the addition of 50 ml. EtOAc, crystals began to form to yield after cooling pure dihydrochloride salt, m.p. 160°-162°; [α]$_D^{25}$-12.75°. A second crop 159°-161° was obtained from the mother liquors.

Anal. Calcd. for C$_{26}$H$_{38}$N$_4$O$_3$: C, 59.20; H, 7.64; N, 10.62, Cl, 13.44. Found: C, 58.95; H, 7.49; N, 10.41; Cl, 13.62.

EXAMPLE 70

(S)-4-(2-Hydroxy-3-isopropylaminopropoxy)phenyl-N-[6-(4-phenyl-1-piperazinyl)hexyl]acetamide and its maleate salt A solution of 7.8 g (R)-4-(2,3-epoxypropoxy)phenyl-4-[6-(4-phenyl-1-piperazinyl)hexyl]acetamide in 175 ml methanol containing 75 ml isopropylamine was heated under reflux for 75 minutes. The solution was evaporated to dryness and the residue was triturated with ether to give the amino-alcohol end product. Crystallization of the product from MeOH-EtOAc furnished pure material, m.p. 103°-104°.

The analytical specimen, m.p. 103°-104°; [α]$_D^{25}$-0.68° (c, 1.0, MeOH) was obtained from the same solvent mixture.

Anal. Calcd. for C$_{30}$H$_{46}$N$_4$O$_3$: C, 70.55; H, 9.08; N, 10.97. Found: C, 70.55; H, 9.06; N, 10.93.

4.4 g (8.615 mmol) of the amine was dissolved in acetone (100 ml) containing 1.0 g (8.615 mmol) of maleic acid. The solution was concentrated to ~75 ml and then was cooled to 0°. The resulting crystalline salt was recovered by filtration to give the maleate, m.p. 107°-108°. Recrystallization from acetone gave the pure salt, m.p. 107°-108°; [α]$_D^{25}$-10.19° (c, 1% MeOH).

Anal. Calcd. for C$_{30}$H$_{46}$N$_4$O$_3$·C$_4$H$_4$O$_4$: C, 65.15; H, 8.04; N, 8.94. Found: C, 65.09; H, 8.15; N, 8.67.

EXAMPLE 71

N-(4-Hydroxyphenyl)-4-phenyl-1-piperazinepropanamide

A solution of 42.0 g (0.259 mol) of 1-phenylpiperazine and 40.0 g (0.245 mol) of N-(4-hydroxyphenyl)-2-propenamide in 600 ml of ethanol was heated under reflux overnight and then cooled. The resulting precipitate was collected and recrystallized from methanol to give the end product as colorless crystals, mp 172°-174°. The analytical sample was obtained by recrystallization from ethanol and had mp 174°-176°.

Anal. Calcd. for C$_{19}$H$_{23}$N$_3$O$_2$: C, 70.13; H, 7.12; N, 12.91. Found: C, 70.22; H, 7.09; N, 12.96.

EXAMPLE 72

(R,S)-N-[4-(3-Chloro-2-hydroxypropoxy)phenyl]-4-phenyl-1-piperazinepropanamide Hydrochloride To a solution of 33.0 g (0.102 mol) of N-(4-hydroxyphenyl)-4-phenyl-1-piperazinepropanamide in 120 ml of 1 N sodium hydroxide was added 50 ml of epichlorohydrin. The reaction was stirred at room temperature overnight and then extracted three times with chloroform. The solvent was removed under vacuum and the crystalline residue was dissolved in 100 ml of concentrated hydrochloric acid. After standing at room temperature for 15 min the solution was concentrated to dryness under vacuum. The residue was recrystallized from methanol using a Soxhlet thimble to give the end product as colorless crystals, mp 242°-244°. Further recrystallization gave the analytical sample, mp 243°-245°.

Anal. Calcd. for C$_{22}$H$_{28}$ClN$_3$O$_3$·HCl: C, 58.15; H, 6.43; Cl, 15.61; N, 9.25. Found: C, 58.16; H, 6.51; Cl, 15.90; N, 9.18.

EXAMPLE 73

(R,S)-N-[4-[3-[(1-Methylethyl)amino]-2-hydroxypropoxy]phenyl]-4-phenyl-1-piperazinepropanamide Bis-Maleate A solution of 2.00 g (0.0044 mol) of (R,S)-N-[4-(3-chloro-2-hydroxypropoxy)phenyl]-4-phenyl-1-piperazinepropanamide hydrochloride and 20 ml of 1-methylethylamine in 20 ml of methanol was heated under reflux for 3 days and then concentrated under vacuum. The residue was mixed with dilute hydrochloric acid and the resulting solution was washed several times with chloroform and then made basic with sodium bicarbonate. The mixture was extracted several times with chloroform and the extracts were dried and concentrated to give (R,S)-N-[4-[3-[1-methylethyl)amino]-2-hydroxypropoxy]-phenyl]-4-phenyl-1-piperazine-propanamide as an amorphous solid. To a methanol solution of 0.80 g (0.0018 mol) of this solid was added 0.42 g (0.0036 mol) of maleic acid. The methanol was removed under vacuum and the residue was recrystallized several times from acetonitrile to give the end product as colorless crystals, mp 159.5°–161.5°.

Anal. Calcd. for $C_{25}H_{36}N_4O_3 \cdot 2C_4H_4O_4$: C, 58.92; H, 6.59; N, 8.33. Found: C, 58.62; H, 6.78; N, 8.36.

EXAMPLE 74

6-Bromo-N-(4-hydroxyphenyl)hexanamide

A mixture of 39.0 g (0.20 mol) of 6-bromohexanoic acid and 39.0 ml of thionyl chloride was heated with a 90° oil bath until the temperature of the mixture had reached 80° and the initial gas evolution had essentially stopped. Excess thionyl chloride was distilled from the reaction mixture under aspirator vacuum. Toluene (25 ml) was added and this also was distilled under aspirator vacuum. The cooled reaction mixture was then added to a slurry of 43.6 g (0.40 mol) of 4-aminophenol in 500 ml of dioxane. After stirring for 30 min the mixture was filtered and the filtrate was concentrated under vacuum. The residue was recrystallized from trichloromethane using a Soxhlet thimble to give the end product as tan crystals, mp 127°–129°. The analytical sample was obtained from dichloromethane with charcoal; colorless crystals, mp 126°–128°.

Anal. Calcd. for $C_{12}H_{16}BrNO_2$: C, 50.36; H, 5.64; Br, 27.93; N, 4.89. Found: C, 50.47; H, 5.69; Br. 27.92; N, 4.68.

EXAMPLE 75

N-(4-Hydroxyphenyl)-4-phenyl-1-piperazinehexanamide

A solution of 45.7 g (0.16 mol) of 6-bromo-N-(4-hydroxyphenyl)hexanamide, 26.0 g (0.16 mol) of 1-phenylpiperazine and 22.4 ml (16.3 g, 0.16 mol) of triethylamine in 400 ml of ethanol was heated under reflux overnight and then concentrated under vacuum. The residue was mixed with sodium bicarbonate solution and trichloromethane. The resulting suspension was filtered. The solid was recrystallized from ethanol-water and then from acetonitrile to give the end product as tan crystals, mp 157°–159°.

Anal. Calcd. for $C_{22}H_{29}N_3O_2$: C, 71.90; H, 7.95; N, 11.43. Found: C, 71.65; H, 7.99; N, 11.38.

EXAMPLE 76

(R,S)-N-[4-[3-[(1-Methylethyl)amino]-2-hydroxypropoxy]phenyl]-4-phenyl-1-piperazinehexanamide A mixture of 38.1 g (0.104 mol) of N-(4-hydroxyphenyl)-4-phenyl-1-piperazinehexanamide and 500 ml of 3 N sodium hydroxide was stirred at room temperature for 45 min. To the resulting solution was added 76 ml of epichlorohydrin and stirring was continued overnight. The heterogeneous reaction mixture was extracted with dichloromethane and the extracts were dried and concentrated to give 45.0 g of an oil. This was absorbed onto a column of 500 g of silica gel. Elution with 7 and 10% ethyl acetate in dichloromethane gave a colorless solid. A solution of 8.8 g of this colorless solid and 50 ml of 1-methylethylamine in 50 ml of methanol was heated under reflux for 4 hr and concentrated under vacuum. The residue was mixed with dichloromethane and sodium bicarbonate solution and the organic layer was dried and concentrated. The residue was precipitated several times from dichloromethane-ether to give the end product as a colorless amorphous solid, mp 125°–130°.

Anal. Calcd. for $C_{28}H_{42}N_4O_3$: C, 69.68; H, 8.77; N, 11.61. Found: C, 69.64; H, 8.48; N, 11.49.

EXAMPLE 77

(R,S)-N-[4-[3-[(1-Methylethyl)amino]-2-hydroxypropoxy]phenyl]-4-phenyl-1-piperazinehexanamide Maleate A methanol solution of 4.10 g (0.0085 mol) of (R,S)-N-[4-[3-[(1-methylethyl)amino]-2-hydroxypropoxy]-phenyl]-4-phenyl-1-piperazinehexanamide and 0.986 g (0.0085 mol) of maleic acid was concentrated and the residue was recrystallized from acetonitrile-ethyl acetate to give the end product as colorless crystals, mp 144.5°–146.5°.

Anal. Calcd. for $C_{28}H_{42}N_4O_3 \cdot C_4H_4O_4$: C, 64.19; H, 7.74; N, 9.36. Found: C, 63.96; H, 7.74; N, 9.29.

EXAMPLE 78

11-Bromo-N-(4-hydroxyphenyl)undecanamide

A mixture of 94.7 g (0.357 mol) of 11-bromoundecanoic acid and 70 ml of thionyl chloride was heated with a 90° oil bath until gas evolution had essentially stopped. Excess thionyl chloride was distilled from the reaction mixture under aspirator vacuum. Toluene (50 ml) was added and this was also distilled under aspirator vacuum. The cooled reaction mixture was then added to a slurry of 78.0 g (0.715 mol) of 4-aminophenol in 500 ml of dioxane. After stirring for 30 min the mixture was filtered and the solid was washed with hot dioxane. The combined filtrates were concentrated and the residue was recrystallized from chloroform to give the end product as colorless crystals, mp 116°–117°.

Anal. Calcd. for $C_{17}H_{26}BrNO_2$: C, 57.30; H, 7.36; Br, 22.43; N, 3.93. Found: C, 57,25; H, 7.28; Br, 22.42; N, 4.17.

EXAMPLE 79

N-(4-Hydroxyphenyl)-4-phenyl-1-piperazineundecanamide

A solution of 66.8 g (0.187 mol) of 11-bromo-N-(4-hydroxyphenyl)undecanamide, 30.3 g (0.187 mol) of 1-phenylpiperazine and 27.0 ml (19.6 g, 0.194 mol) of triethylamine in 600 ml of ethanol was heated under reflux overnight and then cooled. The resulting solid was shaken with sodium bicarbonate solution and dichloromethane and the suspension was filtered. The solid was recrystallized from 95% ethanol to give the end product as colorless crystals, mp 160.5°–162.5°.

Anal. Calcd. for $C_{27}H_{39}N_3O_2$: C, 74.10, H, 8.98; N, 9.60. Found: C, 74.28; H, 8.83; N, 9.42.

EXAMPLE 80

(R,S)-N-[4-[3[(1-Methylethyl)amino]-2-hydroxypropoxy]phenyl]-4-phenyl-1-piperazineundecanamide To a stirring solution of 14.0 g (0.20 mol) of potassium methoxide in 400 ml of methanol was added 44.8 g (0.10 mol) of N-(4-hydroxyphenyl)-4-phenyl-1-piperazineundecanamide. Fifteen minutes later 90 ml of epichlorohydrin was added and stirring was continued overnight. The reaction was concentrated under vacuum and the residue was mixed with sodium bicarbonate solution and extracted with chloroform. The extracts were dried and concentrated and the solid residue was recrystallized from trichloromethane and from ethyl acetate to give 34 g of a colorless solid. This was dissolved in 200 ml of methanol, 200 ml of 1-methylethylamine was added and the solution was heated under reflux overnight and then concentrated under vacuum. The residue was mixed with sodium bicarbonate solution and extracted with chloroform. The extracts were dried and concentrated to give a colorless solid. This was dissolved in chloroform and absorbed onto 500 g of silica gel. Elution with 1:1 methanol/chloroform gave material which upon recrystallization from methanol gave (R,S)-N-[4-[3-[(1-methylethyl)amino]-2-hydroxypropoxy]phenyl]-4-phenyl-1-piperazineundecanamide as colorless crystals, mp 141.5°–142.5°.

Anal. Calcd. for $C_{33}H_{52}N_4O_3$: C, 71.70; H, 9.48; N, 10.13. Found: C, 71.92; H, 9.56; N, 10.04.

EXAMPLE 81

(R,S)-N-[4-[3-[(1-Methylethyl)amino]-2-hydroxypropoxy]phenyl]-4-phenyl-1-piperazineundecanamide Maleate A mixture of 0.200 g (0.36 mmole) of (R,S)-N-[4-[3-[(1-methylethyl)amino]-2-hydroxypropoxy]phenyl]-4-phenyl-1-piperazineundecanamide and 42 mg (0.36 mmole) of maleic acid was recrystallized from methanol-ethyl acetate to give the end product as colorless crystals, mp 141°–142°.

Anal. Calcd. for $C_{33}H_{52}N_4O_3 \cdot C_4H_4O_4$: C, 66.44; H, 8.44; N, 8.38. Found: C, 66,59; H, 8.35; N, 8.28.

EXAMPLE 82

(R,S)-N-[4-[3-[(1-Methylethyl)amino]-2-hydroxypropoxy]-phenyl]-4-phenyl-1-piperazineundecanamide Hydrochloride (1:2)

Hydrogen chloride was bubbled into a solution of 5.53 g (0.010 mol) of (R,S)-N-[4-[3-[(1-methyl ethyl)amino]-2-hydroxypropoxy]phenyl]-4-phenyl-1-piperazineundecanamide in a mixture of dichloromethane and chloroform. The mixture was concentrated under vacuum and the residue was recrystallized from methanolethyl acetate to give the end product, mp 210°–212°.

Anal. Calcd. for $C_{33}H_{52}N_4O_3 \cdot 2HCl$: C, 63.34; H, 8.70; Cl, 11.33; N, 8.95. Found: C, 63.27; H, 8.58; Cl, 11.34; N, 8.79.

EXAMPLE 83

(R,S)-N-[4-[3-[(1-Methylethyl)amino]-2-hydroxypropoxy]phenyl]-4-phenyl-1-piperazinepropanamide To a rapidly stirring solution of 2.243 g (0.01 mol) of 4-[2-hydroxy-3-[(1-methylethyl)amino]propoxy]benzenamine in 100 ml of dichloromethane was added dropwise a solution of 0.80 ml (0.91 g, 0.01 mol) of 2-propenoyl chloride. The reaction was stirred until the intermediate had settled out leaving a clear supernatant which was decanted. The residue was dissolved in 25 ml of ethanol, 5.0 ml (5.3 g, 0.033 mol) of 1-phenylpiperazine was added, and the solution was heated under reflux overnight. The reaction mixture was cooled and filtered. The solid was dissolved in water, and the solution was made basic with sodium bicarbonate and extracted with dichloromethane. The extracts were dried and concentrated and the amorphous residue was reprecipitated several times from ether to give the end product as a colorless amorphous solid, mp 151°–157°. Analyses were performed on this amorphous solid and subsequently the material was obtained crystalline and recrystallized from ether to give the end product as colorless crystals, mp 250°–252°.

Anal. Calcd. for $C_{25}H_{36}N_4O_3$: C, 68.15; H, 8.24; N, 12.72. Found: C, 68.33; H, 8.31; N, 12.65.

EXAMPLE 84

| Tablet Formulations (Wet Formulation) | | |
|---|---|---|
| Ingredients | mg/tablet | mg/tablet |
| (S)-1-[2-(4-(2-hydroxy-3-(1-methylethyl)amino)-propoxy)phenoxy)ethyl]-4-phenylpiperazine bis-maleate salt | 25 | 50 |
| Pregelatinized Starch | 12.5 | 15 |
| Lactose | 155 | 162 |
| AVICEL | 30 | 40 |
| Modified Starch | 25 | 30 |
| Magnesium Stearate | 2.5 | 3 |
| | 250 mg | 300 mg |

Procedure

Mix the first five ingredients in a suitable mixer. Granulate with water and dry in an oven. Mill through a Fitzmill. Add the magnesium stearate and mix for 5 minutes and compress on a suitable tablet press.

EXAMPLE 85

| Tablet Formulation (Direct Compression) | | |
|---|---|---|
| Ingredients | mg/tablet | mg/tablet |
| (S)-1-[2-(4-(2-hydroxy-3-(1-methylethyl)amino)-propoxy)phenoxy)ethyl]-4-phenylpiperazine bis-maleate salt | 25 | 50 |
| Lactose | 147.5 | 157 |
| Modified Starch | 25 | 30 |
| AVICEL | 50 | 60 |
| Magnesium Stearate | 2.5 | 3 |
| | 250 mg | 300 mg |

The first four ingredients are blended in a suitable mixer. The magnesium stearate is thereafter added and mixed for 5 minutes. The mixture is compressed on a suitable tablet press.

EXAMPLE 86

| Capsule Formulation | | |
|---|---|---|
| Ingredients | mg/capsule | mg/capsule |
| (S)-1-[2-(4-(2-hydroxy-3-(1-methylethyl)amino)-propoxy)phenoxy)ethyl]-4-phenylpiperazine bis-maleate salt | 25 | 50 |
| Lactose | 125 | 170 |
| Cornstarch | 40 | 60 |
| Talc | 15 | 20 |
| | 250 mg | 300 mg |

The first three ingredients are blended in a suitable mixer and thereafter the talc is added. The mixture is blended for five minutes and filled on a suitable capsule machine.

EXAMPLE 87

Following the procedures outlined in Examples 84–86, the following preferred compounds and their pharmaceutically acceptable salts may be formulated into tablets or capsules:

(S)-4-[2-hydroxy-3-(1-methylethylamino)propoxy)-phenyl]-N-[2-(4-phenyl-1-piperazinyl)-ethyl]acetamide.

(S)-4-[2-hydroxy-3-(1-methylethylamino)propoxy)-phenyl]-N-[6-(4-phenyl-1-piperazinyl)-hexyl]acetamide.

(S)-1-[6-(4-hydroxy-3-iospropylaminopropoxy)-phenoxy)hexyl]-4-phenylpiperazine.

What is claimed:

1. The compound of the formula

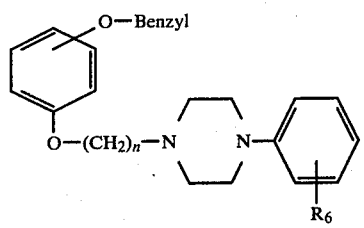

wherein $R_6$ is hydrogen or lower alkoxy and n is 2 to 20.

2. The compound of claim 1 wherein n is 2 to 11.
3. The compound of claim 2 wherein n is 2.
4. The compound of the formula

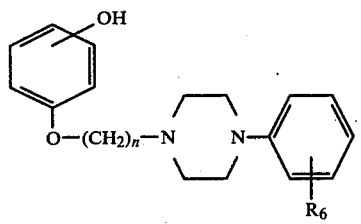

wherein $R_6$ is hydrogen or lower alkoxy and n is 2 to 20.

5. The compound of claim 4 wherein n is 2 to 11.
6. The compound of the formula

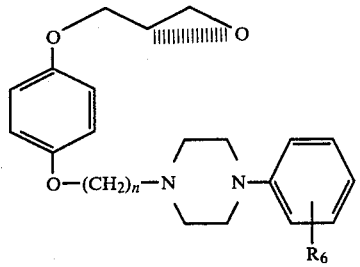

wherein $R_6$ is hydrogen or lower alkoxy and n is 2 to 20.

7. The compound of claim 6 wherein n is 2 to 11.
8. The compound of the formula

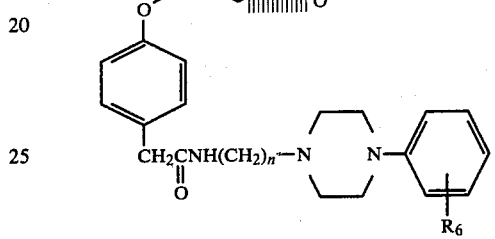

wherein $R_6$ is hydrogen or lower alkoxy and n is 2 to 20.

9. The compound of claim 8 wherein n is 2 to 11.
10. The compound of claim 9 wherein n is 2.
11. The compound of the formula

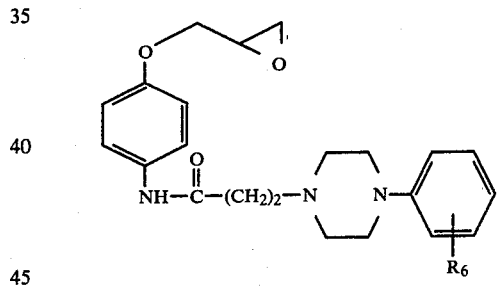

wherein $R_6$ is hydrogen or lower alkoxy.

* * * * *